United States Patent
Torii et al.

(10) Patent No.: US 8,383,746 B2
(45) Date of Patent: Feb. 26, 2013

(54) WATER ABSORBING RESIN WITH IMPROVED INTERNAL STRUCTURE AND MANUFACTURING METHOD THEREFOR

(75) Inventors: Kazushi Torii, Himeji (JP); Hirofumi Shibata, Himeji (JP)

(73) Assignee: Nippon Shokubai Co., Ltd, Osaka (JP)

(*) Notice: Subject to any disclaimer, the term of this patent is extended or adjusted under 35 U.S.C. 154(b) by 893 days.

(21) Appl. No.: 12/294,325

(22) PCT Filed: Mar. 20, 2007

(86) PCT No.: PCT/JP2007/056528
§ 371 (c)(1), (2), (4) Date: Apr. 22, 2009

(87) PCT Pub. No.: WO2007/116778
PCT Pub. Date: Oct. 18, 2007

(65) Prior Publication Data
US 2009/0208748 A1   Aug. 20, 2009

(30) Foreign Application Priority Data

Mar. 27, 2006 (JP) ................................ 2006-085652
Jul. 7, 2006 (JP) ................................ 2006-188668
Sep. 4, 2006 (JP) ................................ 2006-239474

(51) Int. Cl.
C08F 20/06 (2006.01)
(52) U.S. Cl. ........................ 526/317.1; 526/89; 526/213
(58) Field of Classification Search ................ 526/371.1
See application file for complete search history.

(56) References Cited

U.S. PATENT DOCUMENTS

| | | | |
|---|---|---|---|
| 3,935,099 | A | 1/1976 | Weaver et al. |
| 3,959,569 | A | 5/1976 | Burkholder, Jr. |
| 4,076,663 | A | 2/1978 | Masuda et al. |

(Continued)

FOREIGN PATENT DOCUMENTS

| | | |
|---|---|---|
| CA | 2236504 | 5/1997 |
| CA | 2352579 | 6/2000 |

(Continued)

OTHER PUBLICATIONS

Japanese Search Report mailed on Jun. 19, 2007 corresponding to U.S. Appl. No. 12/294,325, filed Sep. 24, 2008.

(Continued)

*Primary Examiner* — Vu A Nguyen
(74) *Attorney, Agent, or Firm* — Turocy & Watson, LLP

(57) ABSTRACT

According to the present invention, the manufacturing method for the water absorbing resin involves the step of polymerizing a water-soluble unsaturated monomer, 0.06 of 5 mol % of which is composed of an internal crosslinking agent; and the step of drying a water-containing gel which has a thermally decomposing radical initiator content index of 40 to 100 at 100 to 250° C. The water absorbing resin of the present invention contains a water-soluble unsaturated monomer as a repeat unit for a major chain, 90 mol % of the monomer being composed of an acrylic acid and/or salt thereof, the resin having an internal crosslinking structure and exhibiting a weight-average molecular weight Mw of 360,000 to 1,000,000 daltons and an intrinsic viscosity IV of 2.1 to 6.0 dL/g where the weight-average molecular weight Mw and the intrinsic viscosity IV are measured after treatment under set 2 of hydrolysis conditions.

7 Claims, 3 Drawing Sheets

U.S. PATENT DOCUMENTS

| | | | |
|---|---|---|---|
| 4,093,776 A | 6/1978 | Aoki et al. |
| 4,124,748 A | 11/1978 | Fujimoto et al. |
| 4,367,323 A | 1/1983 | Kitamura et al. |
| 4,389,513 A | 6/1983 | Miyazaki |
| 4,446,261 A | 5/1984 | Yamasaki et al. |
| 4,625,001 A | 11/1986 | Tsubakimoto et al. |
| 4,654,039 A | 3/1987 | Brandt et al. |
| 4,683,274 A | 7/1987 | Nakamura et al. |
| 4,690,996 A | 9/1987 | Shih et al. |
| 4,721,647 A | 1/1988 | Nakanishi et al. |
| 4,738,867 A | 4/1988 | Itoh et al. |
| 4,748,076 A | 5/1988 | Saotome |
| 4,769,427 A | 9/1988 | Nowakowsky et al. |
| 4,873,299 A | 10/1989 | Nowakowsky et al. |
| 5,250,640 A | 10/1993 | Irie et al. |
| 5,275,773 A | 1/1994 | Irie et al. |
| 5,478,879 A | 12/1995 | Kajikawa et al. |
| 5,849,405 A | 12/1998 | Wang et al. |
| 6,071,976 A | 6/2000 | Dairoku et al. |
| 6,107,358 A | 8/2000 | Harada et al. |
| 2002/0040095 A1 | 4/2002 | Dairoku et al. |
| 2002/0120085 A1 | 8/2002 | Matsumoto et al. |
| 2004/0014901 A1 | 1/2004 | Heide et al. |
| 2005/0003191 A1 | 1/2005 | Ehrnsperger et al. |
| 2005/0228154 A1 * | 10/2005 | Matsumoto et al. ....... 526/317.1 |
| 2006/0276598 A1 | 12/2006 | Wada et al. |
| 2007/0078231 A1 | 4/2007 | Shibata et al. |
| 2007/0106013 A1 | 5/2007 | Adachi et al. |
| 2008/0075937 A1 | 3/2008 | Wada et al. |
| 2008/0119586 A1 | 5/2008 | Byerly et al. |

FOREIGN PATENT DOCUMENTS

| | | |
|---|---|---|
| EP | 0456136 | 11/1991 |
| EP | 0668080 | 8/1995 |
| EP | 1358224 | 11/2003 |
| EP | 1358224 | 12/2004 |
| EP | 1690887 | 8/2006 |
| JP | 11-279288 | 10/1999 |
| JP | 2001-079829 | 3/2001 |
| WO | 2004-066915 | 8/2004 |
| WO | 2004-069915 | 8/2004 |
| WO | 2005-027986 | 3/2005 |
| WO | 2006-109882 | 10/2006 |

OTHER PUBLICATIONS

European Search Report dated Mar. 2, 2009 corresponding to U.S. Appl. No. 12/294,325, filed Sep. 24, 2008.

* cited by examiner

WATER ABSORBING RESIN WITH IMPROVED INTERNAL STRUCTURE AND MANUFACTURING METHOD THEREFOR

TECHNICAL FIELD

The present invention relates in general to water absorbing resins with improved internal structure and manufacturing methods for the resins, and in particular to water absorbing resins and water absorbent cores which are suitably applicable to sanitary/hygienic materials for disposable diapers, sanitary napkins, so-called incontinent pads, and similar goods, and also to manufacturing methods for the water absorbing resins.

BACKGROUND ART

Water absorbent cores containing hydrophilic fiber, such as pulp, and a water absorbing resin are widely used conventionally so that sanitary/hygienic materials, such as disposable diapers, sanitary napkins, and incontinent pads, can absorb body fluids. The water absorbent core is used in sanitary/hygienic materials, such as disposable diapers, sanitary napkins, and incontinent pads, to absorb body fluids.

There are recent demands for these sanitary/hygienic materials to be reduced in thickness for better usability. To this end, water absorbent cores are manufactured with a decreasing ratio of hydrophilic fiber, which has a relatively low bulk density, and an increasing ratio of water absorbing resin, which exhibits excellent water absorption and a relatively high bulk density. The relative quantity of water absorbing resin particles used in the water absorbent core is hence increased, which in turn reduces the thickness of the sanitary/hygienic materials without compromising water absorbency and other physical properties.

The ratio of the hydrophilic fiber may be decreased, but not further below a minimum quantity required. For further reduction in thickness of the sanitary/hygienic materials, the physical properties of the water absorbing resin need to be improved. Examples of such physical properties of the water absorbing resin include centrifuge retention capacity, saline flow conductivity, absorbency against pressure, fixed height absorbency, mass-average particle diameter, and extractable polymer content. The water absorbing resin needs to have these physical properties together in actual use.

These physical properties can be improved by any one of the following four methods: (1) by improving the internal structure of the water absorbing resin, (2) by improving a surface crosslink process, (3) with a liquid permeability improver or other additive, and (4) through the regulation of particle shape and particle size distribution.

Taking the first approach among them, the present invention is intended to improve the internal structure of the water absorbing resin. We have chosen this approach because the improvement of the internal structure is effective not only single handedly, but it also works synergistically with the improvement of the surface crosslink process and the use of additives.

Some technologies are documented that are intended to improve the internal structure. For example, patent document 1 discloses a water absorbing resin that has a particular particle size distribution, particular CRCs, particular AAPs, and a particular chemical crosslink index (or chemical crosslink index under load). The document discloses also a manufacturing method in which a particular polymerization method is used to obtain a water absorbing resin. The resin has a high degree of crosslink, a high retention capacity, and a swelling pressure of gel layer of 35.0 kdyne/cm2 or higher. The resin is processed to exhibit a particular particle size distribution (Particles ranging from 106 μm, inclusive, to 850 μm, exclusive, account for 95 wt % or more of the entire resin content. The particle size distribution has a logarithmic standard deviation σζ of 0.25 to 0.45). After that, the resin is subjected to surface crosslinking, and mixed with a liquid permeability improver. The technology improves gel strength by relatively increasing chemical crosslinking points.

Patent document 2 discloses a method in which alkali metal silicate is added before water-containing gel is dried.

Patent document 3 discloses a method in which two kinds of 2 crosslinking agents are used together.

Patent document 4 discloses a superabsorbent crosslinked polymer material for aqueous liquids which contains a partially neutralized, monoethylenic, unsaturated, acid group-containing monomer, any other monomer copolymerizable with said monomer, and any polymer suited for use as a graft base.

Techniques that are similar to the present invention, but have a different objective are those involving mixing a polymerized water-containing gel with an additive, such as a persulfate. The techniques are intended to lower residual monomers in water absorbing resins and therefore based on a different technical concept from the present invention. The techniques indeed achieve reduction of the residual monomers, but fall short of improving the internal structure of the water absorbing resins due to the quantities of the additives being different and for other reasons. An example of such techniques is the method disclosed in patent document 5. According to the method, a water-containing gel is mixed with fine particles of a water absorbing resin as well as with a polymerization initiator or a reduction agent. Another example is disclosed in patent document 6. According to the method, a water-containing gel is upon comminution mixed with fine particles of a water absorbing resin as well as with a polymerization initiator, such as a persulfate. A further example is disclosed in patent document 7. According to the method, a water-containing gel is mixed with a persulfate. Another example is disclosed in patent document 8 whereby fine particles are upon agglomeration are mixed with a persulfate.

[Patent Document 1] International Application Published under PCT WO2005/27986
[Patent Document 2] European Patent 1137678B1
[Patent Document 3] Specification of U.S. Published Patent Application 2004/0014901
[Patent Document 4] International Application Published under PCT WO97/019116
[Patent Document 5] Japanese Unexamined Patent Publication 05-43610/1993 (Tokukaihei 05-43610)
[Patent Document 6] Japanese Unexamined Patent Publication (Tokukai) 2001-79829
[Patent Document 7] European Patent 1358224B1
[Patent Document 8] European Patent 1690887A

DISCLOSURE OF INVENTION

The above-mentioned conventional techniques have a problem that they cannot deliver a water absorbing resin with necessary physical properties.

Specifically, water absorbing resin is required to exhibit good physical properties (centrifuge retention capacity, saline flow conductivity, absorbency against pressure, fixed height absorbency, mass-average particle diameter, liquid diffusibility, etc.) in the actual use of the water absorbing resin. Conventional technology has so far failed to achieve sufficient values with these physical properties. One factor in the failure is the trade-off between centrifuge retention capacity and saline flow conductivity, both of which are important physical properties for water absorbing resin: if either of the physical properties improves, the other suffers. It is difficult to achieve good values with both of the physical properties.

In addition, although the physical properties of the water absorbing resin improve through polymerization using an additive or by changing internal crosslinking agents, it is a different story whether these approaches would optimize the structure of the water absorbing resin in the first place. It is only through the optimal water absorbing resin structure that one can achieve fundamentally improved physical properties and expect synergistic effects in combinations with conventional art.

The present invention, conceived in view of these conventional issues, has an objective of improving the internal structure of the water absorbing resin and hence fundamentally improving its performance, to provide a water absorbing resin which exhibits high levels of multiple physical properties and a method of manufacturing such a water absorbing resin. Another objective of the present invention is to provide a water absorbent core with an excellent liquid acquisition rate per unit time.

The method of manufacturing a water absorbing resin of the present invention, to address the issues, is a method of manufacturing a water absorbing resin obtained by polymerization of a water-soluble unsaturated monomer, the resin having an internal crosslinking structure, the method involving the steps of:

polymerizing a water-soluble unsaturated monomer; and drying at 100 to 250° C. a water-containing gel which has a thermally decomposing radical initiator content index of 40 to 100, the index being given by:

$$\text{Thermally Decomposing Radical Initiator Content Index} = (Ci/Mi)/(Cm/Mm) \times 10^5$$

where:

Ci is the quantity in mass % of a thermally decomposing radical initiator extracted by stirring the water-containing gel in a 5% aqueous solution of sodium chloride for 1 hour immediately prior to the drying step;

Mi is the mole-average molecular weight in mol/g of the extracted thermally decomposing radical initiator;

Cm is the solid content in mass % of the water-containing gel obtained by drying the water-containing gel at 180° C. for 8 hours; and Mm is the mole-average molecular weight in mol/g of a polymerized monomer.

The above regulation of the thermally decomposing radical initiator content index for the water-containing gel so that it falls within the specified range, and the drying at particular temperatures improve the internal structure of the water absorbing resin. The internal structure of the water absorbing resin is improved presumably because the thermally decomposing radical initiator contained in a particular quantity in the gel upon drying reacts with polymer chains in the water absorbing resin. The improved internal structure in turn improves gel strength and the physical properties listed above.

In addition, the method of manufacturing a water absorbing resin of the present invention is preferably such that the water-soluble unsaturated monomer contains an internal crosslinking agent in an amount of 0.06 to 5 mol %.

The use of a crosslinking agent in polymerization within a particular range of quantity and the drying at a particular range of temperatures of a water-containing gel which has a thermally decomposing radical initiator content index in the above range improves the internal structure of the water absorbing resin. The internal structure of the water absorbing resin is improved presumably because the thermally decomposing radical initiator contained in a particular quantity in the gel upon drying reacts with polymer chains in the water absorbing resin. The improved internal structure in turn improves gel strength and the physical properties listed above.

The water absorbing resin of the present invention, to address the issues, is a water absorbing resin obtained by polymerization of a water-soluble unsaturated monomer, the resin having an internal crosslinking structure and exhibiting an intrinsic viscosity IV of 7.3 dL/g or lower at such a weight-average molecular weight, Mw that Log(Mw)=6.10, where the weight-average molecular weight Mw and the intrinsic viscosity IV are measured after 50 mg of the water absorbing resin is left in 10 grams of a 0.1 mol/L aqueous solution of sodium hydroxide at 80° C. for 3 weeks.

A water absorbing resin with improved internal structure characteristically shows a reduced intrinsic viscosity in a particular range of molecular weight when the resin is decomposed into a polymer in the aqueous solution. This is presumably because the thermally decomposing radical initiator contained in a particular quantity in the gel upon drying reacts with polymer chains in the water absorbing resin, thereby improving the internal structure of the water absorbing resin. The improved internal structure in turn reduces the intrinsic viscosity in a particular range of molecular weight. This characteristic of the water absorbing resin imparts excellent gel strength and the physical properties listed above to the water absorbing resin.

The water absorbing resin of the present invention, to address the issues, is a water absorbing resin containing a water-soluble unsaturated monomer as a repeat unit for a major chain, 90 mol % of the monomer being composed of an acrylic acid and/or salt thereof, the resin having an internal crosslinking structure and exhibiting a weight-average molecular weight Mw of 360,000 to 1,000,000 daltons and an intrinsic viscosity IV of 2.1 to 6.0 dL/g where the weight-average molecular weight Mw and the intrinsic viscosity IV are measured after treatment under set 2 of hydrolysis conditions, in which treatment 20 mg of the water absorbing resin is left in 10 grams of a 0.1 mol/L aqueous solution of sodium hydroxide at 80° C. for 3 weeks.

A water absorbing resin with a further improved internal structure is obtainable by setting the weight-average molecular weight Mw and the intrinsic viscosity IV after the treatment under set 2 of hydrolysis conditions to the specified ranges.

The present invention provides a water absorbing resin with improved internal structure and a manufacturing method therefor. In addition, preferably, the present invention provides a water absorbing resin that has an excellent centrifuge retention capacity CRC, which indicates the amount of absorption by the water absorbing resin, and/or an excellent saline flow conductivity (SFC), which indicates liquid permeability. Thus, there are provided a water absorbing resin and a manufacturing method therefor which boasts an excellent liquid acquisition rate per unit time of the water absorbent core. In addition, preferably, the present invention provides a water absorbing resin that has an excellent absorbency against pressure of 4.83 kPa (AAP). Thus, there are provided a water absorbing resin and a manufacturing method therefor with low liquid seeping, or "rewetting," when the water absorbent core is placed under pressure.

In addition, the present invention provides a water absorbing resin that exhibits an excellent liquid acquisition rate per unit time when used in a water absorbent core. In addition, the present invention provides a water absorbing resin that has a large weight-average molecular weight Mw after hydrolysis and thereby is capable of preserving high water absorption capability in some hydrolysis in actual use.

REFERENCE NUMERALS

Figure 1:
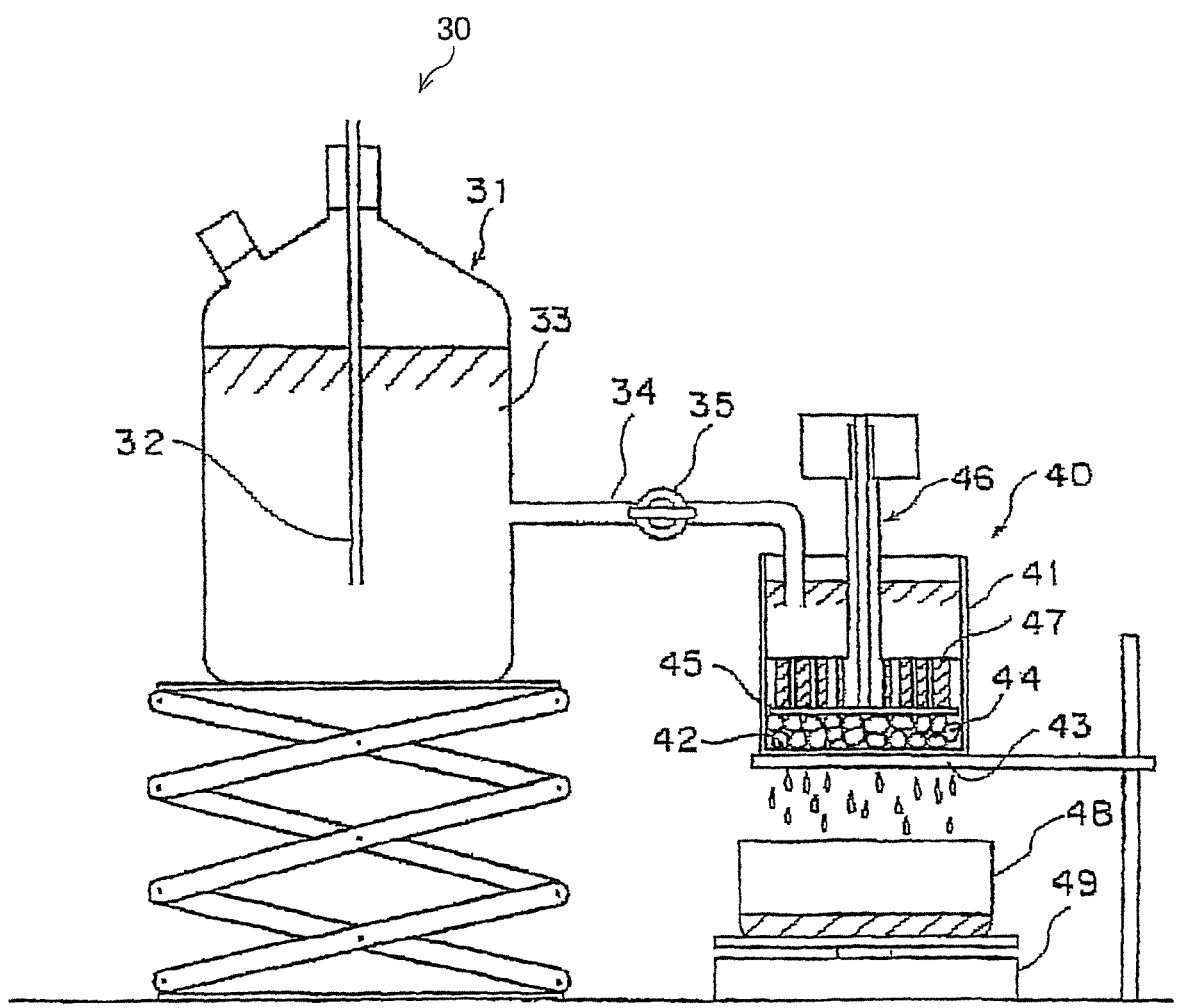
FIG. 1 is a schematic illustration of an apparatus for measuring SFC in accordance with the present example of the invention.

31 Tank
32 Glass Tube
33 0.69 Mass % Saline
34 Valved "L" tube
35 Valve
40 Container
41 Cell
42 Stainless Steel Net
43 Stainless Steel Net
44 Swollen Gel
45 Glass Filter
46 Piston
47 Piston Hole
48 Collector
49 Balance

BEST MODE FOR CARRYING OUT INVENTION

The following will describe the present invention in detail. The scope of the present invention is however not limited by the description. Apart from the examples given below, the invention may be modified in other ways for implementation without departing from the spirit of the invention. Note that in the present invention, "weight" and "mass" are synonyms of "wt %" and "mass %" respectively. Throughout the specification and claims, only "mass" and "mass %" are used.

Abbreviations

Abbreviations which will be used in the following description are defined first.

CRC is an acronym of "centrifuge retention capacity." SFC is an acronym of "saline flow conductivity." AAP refers to absorbency against a pressure of 4.83 kPa. FHA is an acronym of "fixed height absorbency." LDV is an acronym of "liquid distribution velocity." D50 (distribution) refers to a mass-average particle diameter. σζ is the logarithmic standard deviation of a particle size distribution. Saline is an aqueous solution of sodium chloride (0.9% to 0.69%). 1 ppm is equal to 0.0001 mass %.

An embodiment of the present invention is now described.

Polymerization

The water absorbing resin of the present invention is a water absorbing resin, with an internal crosslinking structure, obtained by polymerization of a water-soluble unsaturated monomer (hereinafter, may be referred to simply as a "monomer"). The water absorbing resin used in the present embodiment is a water-insoluble, water-swelling, hydrogel-forming polymer obtained by polymerization of a water-soluble unsaturated monomer (hereinafter, may be referred to as a "water absorbing resin"). In the present invention, a compound containing, as the primary component, 50 to 100 wt %, preferably 70 to 100%, especially preferably 90 to 100% of a water absorbing resin is also referred to as a water absorbing resin even if the compound contains a small quantity of additives or third components, provided that the additives or third components are part of resin particles. "Water insoluble" means that the extractable polymer content (hereinafter, may be referred to as the "water-soluble components"), or the water-soluble polymer, accounts for at least 0 to 50% or less, preferably 25% or less, especially preferably 15% or less.

The "extractable polymer content" refers to the content, of the water absorbing resin, which is soluble in water. The content may be quantified, for example, by the methods outlined later under the heading "Extractable polymer content (Water-soluble Components)."

The content, of the water absorbing resin, which is soluble in water (saline water, preferably 0.9 mass % saline water) is, for example, a polymer content which extracts from water absorbing resin in water over 16 hours of stirring.

Concrete examples of the water-insoluble, water-swelling, hydrogel-forming polymer include partially neutralized, crosslinked polyacrylic acid polymers (Specification of U.S. Pat. No. 4,625,001, Specification of U.S. Pat. No. 4,654,039, Specification of U.S. Pat. No. 5,250,640, Specification of U.S. Pat. No. 5,275,773, Specification of European Patent 456136, etc.); a partially neutralized crosslinked starch-acrylic acid graft polymer (Specification of U.S. Pat. No. 4,076,663); an isobutylene-maleic acid copolymer (Specification of U.S. Pat. No. 4,389,513); a saponification product of a vinyl acetate-acrylic acid copolymer (Specification of U.S. Pat. No. 4,124,748); a hydrolysate of an acrylamide (co) polymer (Specification of U.S. Pat. No. 3,959,569); and a hydrolysate of an acrylonitrile polymer (Specification of U.S. Pat. No. 3,935,099).

The water absorbing resin of the present embodiment is preferably a water absorbing resin containing a polyacrylic acid/polyacrylate-based crosslinked polymer obtained by polymerization of a monomer containing an acrylic acid and/or salt thereof. In the present embodiment, the polyacrylic acid/polyacrylate-based crosslinked polymer refers to the crosslinked polymer obtained by polymerization of a monomer containing an acrylic acid and/or salt thereof in at least 50 mol %, preferably at least 70 mol %, more preferably at least 90 mol %.

Acid groups in the crosslinked polymer are neutralized in a ratio preferably from 50 mol % to 90 mol % inclusive, more preferably from 60 mol % to 80 mol % inclusive. The polyacrylate may be, for example, an alkali metal salt, such as sodium, potassium, or lithium; an ammonium salt; or an amine salt. A preferred example is a sodium salt. The neutralization in which salt is formed may be carried out before the polymerization, that is, in the form of monomer, or during or after the polymerization, that is, in the form of polymer. Alternatively, any of the methods may be used together.

The polyacrylic acid/polyacrylate-based crosslinked polymer that is suited for use as the water absorbing resin of the present embodiment may be prepared by copolymerizing another monomer, if necessary, in addition to the primary component monomer (acrylic acid and/or salt thereof). Concrete examples of the other monomer include unsaturated anionic monomers, such as methacrylic acid, maleic acid, vinyl sulfonic acid, styrene sulfonic acid, 2-(meth)acrylamide-2-methylpropanesulfonic acid, 2-(meth)acryloylethanesulfonic acid, and 2-(meth)acryloylpropanesulfonic acid, and salts thereof; non-ionic hydrophilic group-containing unsaturated monomers, such as acrylamide, methacrylamide, N-ethyl(meth)acrylamide, N-n-propyl(meth)acrylamide, N-isopropyl(meth)acrylamide, N,N-dimethyl(meth) acrylamide, 2-hydroxyethyl(meth)acrylate, 2-hydroxypropyl (meth)acrylate, methoxypolyethylene glycol(meth)acrylate, polyethylene glycol mono(meth)acrylate, vinylpyridine, N-vinylpyrrolidone, N-acryloyl piperidine, N-acryloyl pyrrolidine, and N-vinylacetoamide; and unsaturated cationic monomers, such as N,N-dimethylaminoethyl(meth)acrylate, N,N-diethylaminoethyl(meth)acrylate, N,N-dimethylaminopropyl(meth)acrylate, N,N-dimethylaminopropyl(meth) acrylamide, and quaternary salts thereof. The monomers, other than the acrylic acid and/or salt thereof, may be used in an amount of preferably 0 mol % to 30 mol % inclusive, more preferably 0 mol % to 10 mol % inclusive, to the total amount of the monomers.

The water absorbing resin used in the present embodiment is a crosslinked polymer with an internal crosslinking structure. The internal crosslinking structure may be introduced to the water absorbing resin, for example, through self-crosslinking using no crosslinking agent or by copolymerizing or reacting an internal crosslinking agent containing two or more unsaturated polymerizing groups and/or two or more reactive groups per resin molecule (the copolymerization or reaction of an internal crosslinking agent is preferred).

Concrete examples of the internal crosslinking agent include polyhydric alcohols, such as N,N'-methylene bis (meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerine tri(meth)acrylate, glycerine acrylate methacrylate, ethylene oxide denatured trimethylolpropane tri(meth)acrylate, pentaerythritol tetra(meth)acrylate, dipentaerythritol hexa (meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, 1,4-butanediol, propylene glycol, glycerine, and pentaerythritol; ethylenediamine; polyethyleneimine; and glycidyl(meth)acrylate.

Any one of the internal crosslinking agents may be used alone; alternatively two or more of them may be used. In view of the water absorption property of the obtained water absorbing resin and other factors, a preferred internal crosslinking agent has two or more unsaturated polymerizing groups; a more preferred one has a total of two or more (meth)acrylate groups, allyl groups, or (meth)acrylamide groups; and a still more preferred one has (meth)acrylate groups. The crosslinking agent is preferably soluble in water (solubility is 0.1 g or higher, preferably 1 g or higher; per 100 g of water at 25° C.). Furthermore, the crosslinking agent includes EO structure units, especially, 2-100 EO (ethylene oxide) units.

In the present invention, the internal crosslinking agent is used in an amount of 0.06 to 5 mol % relative to the entire monomer content before the polymerization step to improve the internal structure of the water absorbing resin. If less than or equal to 0.06 mol % is used, a large amount of uncrosslinked polymer occurs when a thermally decomposing radical initiator reacts during drying. That may cause increase in the extractable polymer content, which in turn reduces gel strength. Preferably, the amount of the internal crosslinking agent used is from 0.07 to 3 mol %, more preferably from 0.08 to 1 mol %, and most preferably from 0.09 to 0.5 mol %.

In the polymerization step, a hydrophilic polymer, such as starch-cellulose, a derivative of starch-cellulose, polyvinyl alcohol, polyacrylic acid (salt), or a crosslinked polymer of polyacrylic acid (salt), may be added in, for example, 0 to 30 wt % (relative to the monomer). Also in the polymerization, a chain transfer agent, such as hypophosphorous acid (salt), may be added in, for example, 0 to 1 wt % (relative to the monomer).

The monomer containing the above-mentioned acrylic acid and/or salt thereof as the primary component(s) can be polymerized in the polymerization step by bulk polymerization, reverse suspension polymerization, or precipitation polymerization. Nevertheless, solution polymerization, using the monomer dissolved or dispersed in water, is preferred in view of performance and ease in controlling the polymerization. These polymerizations are described in, for example, the Specification of U.S. Pat. No. 4,625,001, the Specification of U.S. Pat. No. 4,769,427, the Specification of U.S. Pat. No. 4,873,299, the Specification of U.S. Pat. No. 4,093,776, the Specification of U.S. Pat. No. 4,367,323, the Specification of U.S. Pat. No. 4,446,261, the Specification of U.S. Pat. No. 4,683,274, the Specification of U.S. Pat. No. 4,690,996, the Specification of U.S. Pat. No. 4,721,647, the Specification of U.S. Pat. No. 4,738,867, the Specification of U.S. Pat. No. 4,748,076, and the Specification of U.S. Published Patent Application 2002/40095.

In the polymerization step, a radical polymerization initiator, such as potassium persulfate, ammonium persulfate, sodium persulfate, t-butylhydroperoxide, hydrogen peroxide, or 2,2'-azobis(2-amidino propane)dihydrochloride, or an activation energy beam, such as an ultraviolet or electron beam, may be used.

In the case of using the radical polymerization initiator, redox polymerization may be carried out by using in combination with a reduction agent, such as sodium sulfite, sodium hydrogen sulfite, ferrous sulfate, or L-ascorbic acid. Preferably, however, a thermally decomposing, water-soluble radical polymerization initiator (solubility is 1 g or higher, preferably 10 g or higher, per 100 g of water at 25° C.), chosen from azo compounds and peroxides, is used.

The radical initiator is preferably added to a reaction system for the polymerization step. The "reaction system for the polymerization step" refers to a reaction system, capable of producing a water-containing gel, in which the water-soluble unsaturated monomer could be polymerized. Therefore, the reaction system for the polymerization step is not limited in any particular manner so long as it includes a water-soluble unsaturated monomer. The system may include an internal crosslinking agent, a chain transfer agent, or a a-hydroxy carboxylic acid (salt), to name a few examples.

The radical polymerization initiator may be added before and/or during the polymerization step, not after the polymerization step.

Throughout this specification, "before the polymerization step" refers to the time before the water-soluble unsaturated monomer starts polymerization. "During the polymerization step" refers to the period from the time when the water-soluble unsaturated monomer starts polymerization to the time when the polymerization terminates. "After the polymerization step" refers to the time after the polymerization of the water-soluble unsaturated monomer terminates.

Whether or not the water-soluble unsaturated monomer has started polymerization is determined through a rise in temperature of the produced polymer. Specifically, it is determined that the water-soluble unsaturated monomer has started polymerization when the rise in temperature has reached 3° C. (preferably 5° C.).

Whether or not the polymerization of the water-soluble unsaturated monomer has terminated is determined according to whether the rise in temperature in polymerization has or has not reached a peak and whether the remaining monomer has or has not reduced to 5 mass % or less.

The addition of the radical polymerization initiator to the reaction system for the polymerization step before the polymerization step and/or during the polymerization step causes a particular amount of the radical initiator to remain inside the water-containing gel. In addition, when the water-containing gel is dried, the particular amount of the radical initiator works on polymer chains in the water absorbing resin, thereby improving the internal structure of the water absorbing resin.

The radical polymerization initiator (especially, the thermally decomposing radical initiator) is used preferably in 0.051 to 1.000 mol % or less, more preferably in 0.054 to 0.2000 mol %, and most preferably in 0.058 to 0.1000 mol %, relative to the entire monomer content.

The polymerization is preferably performed in the presence of an α-hydroxy carboxylic acid (salt) in the present invention, which prevents the water absorbing resin from being colored. The hydroxy carboxylic acid is a carboxylic acid containing a hydroxyl group in a molecule. Examples of such acids include lactic acid, glycolic acid, malic acid, glyceric acid, tartaric acid, citric acid, isocitric acid, salicylic acid, mandelic acid, gallic acid, mevalonic acid, quinic acid, shikimic acid, and β-hydroxy propionic acid.

Among the compounds, the α-hydroxy carboxylic acid, used in the present invention, refers to the carboxylic acid in which a hydroxyl group is bonded to the carbon at an α site in a molecule. The acid is preferably a non-polymer α-hydroxy carboxylic acid and has a weight-average molecular weight of 40 to 2000, more preferably 60 to 1000, and still more preferably 100 to 500. Also, the acid is preferably water-soluble. Examples of the α-hydroxy carboxylic acid include lactic acid (salt), citric acid (salt), malic acid (salt), isocitric acid (salt), glyceric acid (salt), and polyα-hydroxy acrylic acid (salt). Those α-hydroxy carboxylic acids which are especially preferred among them are lactic acid and α-hydroxy polycarboxylic acids which contain two or more carboxyl groups, preferably 2 to 10, more preferably, 2 to 6, even more preferably 2 to 4, in a single molecule. Malic acid (salt) and citric acid (salt) are most preferably used in view of water absorption and improvement in the coloring problem.

If the α-hydroxy carboxylic acid is a salt in the present invention, the acid is preferably a monovalent salt of an alkali metal, such as lithium, potassium, and sodium, ammonia, or amine in view of solubility water. If the α-hydroxy polycarboxylic acid is used as a salt, either all or some of the carboxyl groups may be turned into salt.

The α-hydroxy carboxylic acid, preferably the α-hydroxy polycarboxylic acid, used in the present invention may be used normally in an amount of 0.01 to 10 mass %, preferably 0.05 to 5 mass %, more preferably 0.1 to 3 mass %, and most preferably 0.2 to 3 mass % relative to the water-soluble unsaturated monomer or the associated polymer, in view of water absorption and coloring prevention.

In the present invention, it takes preferably 20 minutes or less, more preferably 15 minutes or less, for the polymer temperature to reach a maximum since the start of the polymerization (determined in terms of temperature rises, viscosity rises, and whitening). Through these time range settings, the resultant thermally decomposing radical initiator content index readily falls in a preferred range.

In the present invention, the thermally decomposing radical initiator content index can be made to fall in the preferred range by adjusting, to a given value, the time taken by the polymer to become dried after its temperature has reached the maximum. The atmospheric temperature during that period of time is also adjustable to a given value to make the thermally decomposing radical initiator content index fall into the preferred range.

Water-Containing Gel

In the present invention, the thermally decomposing radical initiator content index is regulated to 40 to 100. The index is given by the equation below from "Ci," "Mi," "Cm," and "Mm." Ci is the quantity in mass % of a thermally decomposing radical initiator extracted by stirring a water-containing gel in a 5% aqueous solution of sodium chloride for 1 hour immediately prior to the drying step. Mi is the mole-average molecular weight in mol/g of the extracted thermally decomposing radical initiator. Cm is the solid content in mass % of the water-containing gel obtained by drying the water-containing gel at 180° C. for 8 hours. Mm is the mole-average molecular weight in mol/g of a polymerized monomer. The thermally decomposing radical initiator content index is preferably from 41 to 80, and most preferably from 42 to 80.

$$\text{Thermally Decomposing Radical Initiator Content Index} = (Ci/Mi)/(Cm/Mm) \times 10^5$$

where:

Ci is the quantity in mass % of a thermally decomposing radical initiator extracted by stirring a water-containing gel in a 5% aqueous solution of sodium chloride for 1 hour immediately prior to the drying step;

Mi is the mole-average molecular weight in mol/g of the extracted thermally decomposing radical initiator;

Cm is the solid content in mass % of the water-containing gel obtained by drying the water-containing gel at 180° C. for 8 hours; and Mm is the mole-average molecular weight in mol/g of a polymerized monomer.

We have found that the above regulation of the thermally decomposing radical initiator content index for the water-containing gel so that it falls within the specified range, and the drying at particular temperatures improve the internal structure of the water absorbing resin, thereby greatly improving various physical properties, which has led to the completion of the invention. If the index is less than 40, the internal polymer chain of the water absorbing resin may experience little change, possibly failing to achieve sufficient improvement effects. That raises possibility that the physical properties may not be improved. If the index is greater than 100, the internal polymer chain of the water absorbing resin may go under excess change and suffer damage. That can increase the extractable polymer content, possibly failing to achieve improvement in the physical properties. The thermally decomposing radical initiator is preferably the above-mentioned radical initiator, most preferably a persulfate.

When samples are prepared of the water-containing gel immediately prior to the drying step, if necessary, the particle diameter should be adjusted to 5 mm, preferably to shorter than or equal to 3 mm, and the samples then be immediately placed in an atmosphere at −25° C. for rapid cooling before the measurement of the numeric values. These precautions prevents decomposition of the thermally decomposing radical initiator.

The water absorbing resin of the present invention changes its solubility during the course of the treatment by preferably 10 to 100 wt %, more preferably 30 to 95 wt %, and even more preferably 50 to 90 wt %. The solubility after the treatment is preferably 50 to 100 wt %, more preferably 70 to 100 wt %, and even more preferably 90 to 100 wt %.

After the polymerization according to the present invention, the water-containing gel before the drying contains preferably 10 mass % or less, more preferably 7 mass % or less, and most preferably 5 mass % less unreacted monomer. Accordingly, the improvement of the internal structure of the water absorbing resin, which occurs during the drying, is presumably less likely to be disrupted by the unreacted monomer. The ratio of the unreacted monomer does not need to be lowered further than about 0.01%, or more preferably 0.1%.

After the polymerization according to the present invention, the solid content (measured by the method which will be detailed later) in the water-containing gel before the drying is preferably 10 to 80 mass %, more preferably 20 to 70 mass %, and most preferably 30 to 60 mass %. After the polymerization according to the present invention, the water-containing gel before the drying preferably contains the above-mentioned α-hydroxy carboxylic acid (salt).

Drying

In the case where the crosslinked polymer is obtained by solution polymerization and is in the form of gel, in other words, where the crosslinked polymer is a crosslinked polymer in the form of a water-containing gel (hereinafter may be referred to simply as "water-containing gel"), the crosslinked polymer is dried and usually pulverized/crushed before and/or after the drying, to produce the water absorbing resin. In the present invention, drying is an operation of increasing the solid content of a gel-like substance until it becomes like powder. Typically, the content is increased up to 90% or higher, preferably 93%- or even higher, more preferably 95% or higher. There is no need to exceed about 99%. The drying may be performed simultaneously with the polymerization. Preferably, however, there is provided a drying step (drying device) after the polymerization.

In the present invention, the drying is performed at 100° C. to 250° C. at 50% or more, especially, substantially all. At temperatures below 100° C., the internal polymer chain of the water absorbing resin may experience little change, possibly failing to achieve sufficient improvement effects. That raises possibility that the physical properties may not be improved. At temperatures above 250° C., the water absorbing resin may suffer damage. That can increase the extractable polymer content, possibly failing to achieve improvement in the physical properties. The drying temperature is specified in terms of the temperature of a heat medium. If the drying temperature cannot be specified in terms of heat medium temperature as in the case of microwave drying, the drying temperature is specified in terms of material temperature. There is no particularly preferred drying method, so long as the parameters fall in the above-mentioned ranges. Possible examples would be windless drying, depressurized drying, infrared drying, and microwave drying. Hot wind drying is preferred. The dry air flow rate is preferably from 0.01 to 10 m/sec, more preferably from 0.1 to 5 m/sec.

The drying temperature is more preferably from 130° C. to 220° C., most preferably from 150° C. to 200° C. The temperature may be either constant or varied. In any case, almost all the drying step(s) should be preferably performed at the above-mentioned temperature.

The drying time, which may vary depending on the surface area of the polymer, water content, and the type of drier, is determined to achieve the target water content. The drying time is preferably 10 to 120 minutes, more preferably 20 to 90 minutes, most preferably 30 to 60 minutes. With a drying time shorter than 10 minutes, the internal polymer chain of the water absorbing resin may experience little change, possibly failing to achieve sufficient improvement effects. That raises possibility that the physical properties may not be improved. With a drying time in excess of 120 minutes, the water absorbing resin may suffer damage. That can increase the extractable polymer content, possibly failing to achieve improvement in the physical properties.

In the present invention, the solid content (measured by the method which will be detailed later) in the water absorbing resin after the drying is preferably 90 mass % or higher, most preferably 95 mass % or higher. If the solid content is low, fluidity falls, causing difficulty in manufacturing: the water absorbing resin may not be pulverizable, or a particular particle size distribution may not be achievable. In addition, the internal polymer chain of the water absorbing resin may experience little change, possibly failing to achieve sufficient improvement.

Pulverization & Classification

The dried substance obtained according to the above-mentioned method of manufacturing a water absorbing resin is pulverized in a pulverizer. The pulverizer is not limited in any particular manner. Examples include a roll-using pulverizer like a roll mill; a hammer-using pulverizer like a hammer mill; an impact applying pulverizer, a cutter mill, a turbo grinder, a ball mill, and a flush mill. Among them, the roll mill is preferred for the control of a particle size distribution. The pulverization may be performed successively twice or more times (preferably three or more times) for the control of a particle size distribution. If the pulverization is performed twice or more, the same pulverizer or different pulverizers may be used. Different types of pulverizers may also be used in any combination.

The pulverized water absorbing resin may be subjected to classification using sieves with particular mesh sizes to give the resin a particular particle size distribution. The classifier is not limited in any particular manner. Examples include a vibration sieve (unbalance weight drive type, resonance type, vibration motor type, electromagnetic type, disc vibration type, etc.), an in-plane motion sieve (horizontal motion type, horizontal circular-straight line motion type, three-dimensional circular motion type, etc.), a movable net type sieve, a forced stirring type sieve, a net surface vibration type sieve, a wind force sieve, and a sonic wave sieve. The vibration sieve and the in-plane motion sieve are preferred. The mesh is preferably from 1000 μm to 300 μm, more preferably from 900 μm to 400 μm, and most preferably from 710 μm to 450 μm. If the mesh is out of these ranges, the target particle size distribution may be unobtainable.

For the purpose of giving the resin a particular particle size distribution, the water absorbing resin of the present invention may be subjected to further classification to remove some or all of the particles smaller than a particular diameter. The classifier is not limited in any particular manner in the current step. Preferable examples include fine particle classification devices (centrifugal force types, inertia force types, etc.), as well as those listed above. The current step removes some or all of the particles with diameters of preferably 200 μm or less, more preferably 150 μm or less, and most preferably 106 μm or less.

The water absorbing resin obtained by the polymerization explained above is typically granulated particles or primary particles (single particles) of which the shape is, for instance, irregularly pulverized, spherical, fibrous, virgate, substantially spherical, or flat. It is preferred if the resin has an irregularly pulverized shape because the resin can be readily fixed when, for example, used in a water absorbent core.

Surface Crosslinking

The water absorbing resin according to the present embodiment preferably has its surface and nearby regions crosslinked by an organic surface crosslinking agent and/or a water-soluble inorganic surface crosslinking agent. In other words, the method of manufacturing a water absorbing resin according to the present invention preferably involves a step of surface crosslinking the dried water absorbing resin.

Having its surface and nearby regions crosslinked by the surface crosslinking agent, the water absorbing resin causes less liquid seeping when swollen and placed under pressure. The resin hence shows greater AAP and SFC values. As a result, the water absorbing resin, when used in a water absorbent core, causes low liquid seeping, or "rewetting," under pressure and provides a water absorbent core with an excellent liquid acquisition rate per unit time.

Examples of the surface crosslinking agent that can be used in the surface crosslinking include organic surface crosslinking agents and/or water-soluble inorganic surface crosslinking agents with two or more functional groups which can react with the functional groups, especially, carboxyl groups, of the water absorbing resin. Water-soluble organic surface crosslinking agents are preferred.

Examples include polyhydric alcohols, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerine, polyglycerine, 2-butene-1,4-diol, 1,3-butanediol, 1,4-butanediol, 1,5-pentanediol, 1,6-hexanediol, 1,2-cyclohexane dimethanol, 1,2-cyclohexanol, trimethylolpropane, diethanol amine, triethanol amine, polyoxypropylene, oxyethylene-oxypropylene block copolymer, pentaerythritol, and sorbitol; epoxy compounds, such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyvalent amine compounds, such as ethylenediamine, diethylenetriamine, triethylenetetramine, tetraethylenepentamine, pentaethylenehexamine, and polyethyleneimine, and their inorganic and organic salts (for example, azetidinium salts); polyvalent isocyanate compounds, such as 2,4-tolylenediisocyanate and hexamethylenediisocyanate; polyvalent oxazoline compounds, such as 1,2-ethylenebisoxazoline; derivatives of carbonic acids, such as urea, thiourea, guanidine, dicyandiamide, and 2-oxazolidinone; alkylene carbonate compounds, such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxy methyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; haloepoxy compounds, such as epichlorohydrin, epibromohydrin, and α-methylepichlorohydrin, and their polyvalent amine adducts (for example, Kymene (Registered Trademark) manufactured by Hercules Incorporated; silane coupling agents, such as γ-glycidoxypropyl trimethoxysilane and γ-aminopropyl triethoxysilane; and oxetane compounds, such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol, 3-chloromethyl-3-methyl oxetane, 3-chloromethyl-3-ethyl oxetane, and polyvalent oxetane compounds.

Any one of these surface crosslinking agents may be used alone; alternatively two or more of them may be used together. Among them, polyhydric alcohols are preferred because they are very safe and capable of improving the hydrophilicity of the water absorbing resin surface.

The surface crosslinking agent is used preferably in an amount of from 0.001 mass parts to 5 mass parts inclusive, relative to 100 mass parts of the solid content of the water absorbing resin.

Water may be used in mixing the surface crosslinking agent with the water absorbing resin. The water is used in an amount of preferably from 0.5 mass parts, exclusive, to 10 mass parts, inclusive, and more preferably from 1 mass part to 5 mass parts, both inclusive, relative to 100 mass parts of the solid content of the water absorbing resin.

A hydrophilic organic solvent or a third substance may be used as an auxiliary agent when mixing a surface crosslinking agent or its aqueous solution with the water absorbing resin. Examples of such hydrophilic organic solvents include lower alcohols, such as methyl alcohol, ethyl alcohol, n-propyl alcohol, isopropyl alcohol, n-butyl alcohol, isobutyl alcohol, and t-butyl alcohol; ketones, such as acetone; ethers, such as dioxane, tetrahydrofuran, and methoxy (poly)ethylene glycol; amides, such as ε-caprolactam and N,N-dimethyl formamide; sulfoxides, such as dimethyl sulfoxide; and polyhydric alcohols, such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerine, polyglycerine, 2-butene-1,4-diol, 1,3-butanediol, 1,4-butanediol, 1,5-pentanediol, 1,6-hexanediol, 1,2-cyclohexane dimethanol, 1,2-cyclohexanol, trimethylolpropane, diethanol amine, triethanol amine, polyoxypropylene, oxyethylene-oxypropylene block copolymer, pentaerythritol, and sorbitol.

The hydrophilic organic solvent may be used in an amount preferably 10 mass parts or less, and more preferably from 0 mass parts to 5 mass parts, both inclusive, relative to 100 mass parts of the solid content of the water absorbing resin. That amount however may vary depending on the type, particle diameter, and water content of the water absorbing resin, as well as other factors.

The third substance may be, for instance, the inorganic, organic, or polyamino acid described in the Specification of European Patent 0668080. The auxiliary mixed agent may act as a surface crosslinking agent, but preferably should not adversely affect the water absorption capability of the water absorbing resin after the surface crosslinking. The water absorbing resin of the present embodiment is preferably crosslinked by mixing the resin with a surface crosslinking agent containing no hydrophilic organic solvent of which the boiling point is 100° C. or below and then heating the mixture. If the water absorbing resin contains a hydrophilic organic solvent of which the boiling point is 100° C. or below, the hydrophilic organic solvent may vaporize, changing the environment in which the surface crosslinking agent resides on the surface of the water absorbing resin. One may not achieve sufficient SFC or other physical properties.

When the surface crosslinking agent is mixed with the water absorbing resin, preferably, a water-soluble inorganic salt (preferably a persulfate) is also present to obtain a more uniform mixture of the water absorbing resin and the surface crosslinking agent. The water-soluble inorganic salt is used in an amount of preferably from 0.01 mass parts to 1 mass part inclusive, and more preferably from 0.05 mass parts to 0.5 mass parts inclusive, relative to 100 mass parts of the solid content of the water absorbing resin. The amount however may vary depending on the type and particle diameter of the water absorbing resin, as well as other factors. In other words, the water absorbing resin of the present embodiment is preferably crosslinked by mixing the resin with an organic surface crosslinking agent and/or a water-soluble inorganic surface crosslinking agent containing a water-soluble inorganic salt (preferably a persulfate) in a ratio of 0.01 mass % to 1.0 mass %, inclusive, to the water absorbing resin and then heating the mixture.

The method for mixing the surface crosslinking agent with the water absorbing resin is not limited in any particular manner. For example, the water absorbing resin may be immersed in a hydrophilic organic solvent and mixed with a surface crosslinking agent dissolved, as necessary, in water and/or a hydrophilic organic solvent. Another mixing method example may be to directly spray or add dropwise to the water absorbing resin a surface crosslinking agent dissolved in water and/or a hydrophilic organic solvent.

After mixing the surface crosslinking agent with the water absorbing resin, heat is usually and preferably applied so that the crosslink reaction can proceed. The heat treatment temperature (heat medium temperature), although variable depending on the surface crosslinking agent being used, is preferably from 40° C. to 250° C. inclusive, and more preferably from 150° C. to 250° C. inclusive. If the heat treatment temperature is lower than 40° C., the AAP, SFC, and other absorption properties may not be sufficiently improved. If the heat treatment temperature is higher than 250° C., the excess heat may degrade the water absorbing resin and hence various physical properties; care should be taken. The heat treatment time is preferably from 1 minute to 2 hours inclusive, and more preferably from 5 minutes to 1 hour inclusive. Preferably, the surface crosslinking is performed in the presence of the α-hydroxy carboxylic acid (salt) mentioned above, in which case the water absorbing resin is prevented from being colored.

Salt of Polyvalent Metal and Other Additives

The method of manufacturing a water absorbing resin according to the present invention preferably involves a step of adding a polyvalent metal salt to the water absorbing resin (preferably to the particle surface), especially, in or after the surface crosslinking. The polyvalent metal salt is added in an amount of preferably from 0.001 mass % to 5 mass % inclusive, and more preferably from 0.01 mass % to 1 mass % inclusive, relative to the water absorbing resin.

Due to the addition of the polyvalent metal salt (preferably a water-soluble trivalent metal salt), the water absorbing resin of the present invention shows improved saline flow conductivity SFC while substantially preserving its absorbency under the pressure of 4.83 kPa AAP and fixed height absorbency FHA.

Concrete examples of the polyvalent metal salt that can be used in the present invention include a sulfate, nitrate, carbonate, phosphate, organic acid salt, halide (e.g., chloride) of a metal selected from Zn, Be, Mg, Ca, Sr, Al, Fe, Mn, Ti, Zr, Ce, Ru, Y, and Cr as examples. Other examples are those polyvalent metal salts described in Japanese Unexamined Patent Publication (Tokukai) 2005-11317.

Among the polyvalent metal salts, water-soluble trivalent metal salts are the most preferred. Concrete examples of the water-soluble trivalent metal salts include aluminum chloride, aluminum polychloride, aluminum sulfate, aluminum nitrate, aluminum potassium sulfate, aluminum sodium sulfate, potassium alum, ammonium alum, sodium alum, sodium aluminate, iron(III) chloride, cerium(III) chloride, ruthenium(III) chloride, yttrium(III) chloride, and chromium (III) chloride.

It is preferable to use these salts which contain crystal water in view of the solubility of urine and other liquids absorbed. Preferred among them are aluminum compounds, especially, aluminum chloride, aluminum polychloride, aluminum sulfate, aluminum nitrate, aluminum potassium sulfate, aluminum sodium sulfate, potassium alum, ammonium alum, sodium alum, and sodium aluminate. Aluminum sulfate is particularly preferred. The most preferred is an aqueous solution of aluminum sulfate (desirably, a solution of aluminum sulfate with a 90% or higher concentration as based on saturation). Any one of these compounds may be used alone; alternatively two or more of them may be used together.

The method of manufacturing a water absorbing resin according to the present invention preferably involves a step of adding the α-hydroxy carboxylic acid (salt) named above. The addition prevents the water absorbing resin from being colored. The α-hydroxy carboxylic acid (salt) should be added to the water absorbing resin in an amount of 0.1 to 10 mass %, preferably 0.1 to 5 mass %, more preferably 0.15 to 3 mass %, and most preferably 0.2 to 3 mass %, relative to the water absorbing resin. If the amount of the α-hydroxy carboxylic acid (salt) is out of the ranges, it becomes difficult to strike a good balance between water absorption properties (especially, SFC) and coloring prevention.

The polyvalent metal salt and/or the α-hydroxy carboxylic acid (salt), when mixed with the water absorbing resin, is/are preferably provided in the form of an aqueous solution. The concentration of the water-soluble polyvalent metal salt in an aqueous solution containing the polyvalent metal salt is preferably 50% or higher, more preferably 60% or higher, even more preferably 70% or higher, still more preferably 80% or higher, and further preferably 90% or higher, as based on saturation, to prevent the infiltration and diffusion into the water absorbing resin. The concentration may equal the saturation concentration. Besides, the aqueous solution which contains at least the polyvalent metal salt may also contain an organic acid or salt thereof (preferably the α-hydroxy carboxylic acid (salt)), such as the hydrophilic organic solvent and lactic acid (or salt thereof). The addition of the organic acid or salt is preferable because at least the polyvalent metal salt is restrained from infiltrating or diffusing into the water absorbing resin, and the compounds are better mixed.

Water Absorbing Resin

The water absorbing resin of the present invention is a water absorbing resin obtained by polymerization of a water-soluble unsaturated monomer, the resin having an internal crosslinking structure and exhibiting an intrinsic viscosity IV of 7.3 dL/g or lower, more preferably 7.25 dL/g or lower, and most preferably 7.2 dL/g or lower, at such a weight-average molecular weight Mw that Log(Mw)=6.10, where the weight-average molecular weight Mw and the intrinsic viscosity IV are measured after leaving 50 mg of the water absorbing resin in 10 grams of a 0.1 mol/L aqueous solution of sodium hydroxide at 80° C. for 3 weeks. The minimum intrinsic viscosity IV is preferably 4 dL/g or higher, more preferably 5 dL/g or higher, and most preferably 6 dL/g or higher. A measurement method will be described later in detail.

The water absorbing resin of the present invention has a weight-average molecular weight in logarithm (Log(Mw)) of preferably 5.7 to 6.5, more preferably 5.8 to 6.3, and most preferably 5.9 to 6.2, after the treatment. Out of the ranges, the feature represented by the intrinsic viscosity may not show up. In other words, The weight-average molecular weight in logarithm (Log(Mw)) falling in the above-mentioned ranges makes it easier to produce effective internal structure improvement with the water absorbing resin.

The water absorbing resin of the present invention is a water absorbing resin containing a water-soluble unsaturated monomer as a repeat unit for a major chain, 90 mol % of the monomer being composed of an acrylic acid and/or salt thereof, the resin having an internal crosslinking structure and exhibiting a weight-average molecular weight Mw of 360,000 to 1,000,000 daltons, preferably 370,000 to 700,000 daltons, most preferably 380,000 to 500,000 daltons, and an intrinsic viscosity IV of 2.1 to 6.0 dL/g, preferably 2.15 to 4.0 dL/g, more preferably 2.2 to 3.0 dL/g, most preferably 2.25 to 2.6 dL/g, where the weight-average molecular weight Mw and the intrinsic viscosity IV are measured after treatment under set 2 of hydrolysis conditions (will be described later).

The treatment under set 2 of hydrolysis conditions is a treatment in which 20 mg of the water absorbing resin is left in 10 g of a 0.1 mol/L aqueous solution of sodium hydroxide at 80° C. for 3 weeks. The weight-average molecular weight Mw and the intrinsic viscosity IV are measured after the treatment. A measurement method will be described later in detail. A water absorbing resin with a further improved internal structure is obtainable by setting the weight-average molecular weight Mw and the intrinsic viscosity IV after the treatment under set 2 of hydrolysis conditions to the specified ranges.

The molecular weight distribution Mw/Mn after the treatment under set 2 of hydrolysis conditions of the present invention is preferably from 2.0 to 3.0, more preferably from 2.1 to 2.8, most preferably from 2.2 to 2.6. A water absorbing resin with a further improved internal structure is obtainable by setting the molecular weight distribution Mw/Mn after the treatment under set 2 of hydrolysis conditions to the specified range.

The water absorbing resin of the present invention has a CRC of preferably 5 g/g or greater, more preferably 15 g/g or greater, even more preferably 25 g/g or greater, and still more preferably 28 g/g or greater. The maximum CRC, although not limited in any particular manner, is preferably 50 g/g or less, more preferably 45 g/g or less, and even more preferably 40 g/g or less. If the CRC is less than 5 g/g, the water absorbing resin, used in a water absorbent core, absorbs too small an amount of liquid to be used as diapers and other sanitary/hygienic materials. If the CRC is greater than 50 g/g, the water absorbing resin, used in the water absorbent core, may not exhibit an excellent liquid acquisition rate to the water absorbent core per unit time.

The water absorbing resin of the present invention has a SFC of preferably 10 ($10^{-7} \cdot cm^3 \cdot s \cdot g^{-1}$) or greater, more preferably 30 ($10^{-7} \cdot cm^3 \cdot s \cdot g^{-1}$) or greater, even more preferably 50 ($10^{-7} \cdot cm^3 \cdot s \cdot g^{-1}$) or greater, still more preferably 70 ($10^{-7} \cdot cm^{30} \cdot s \cdot g^{-1}$) or greater, and the most preferably 100 ($10^{-7} \cdot cm^3 \cdot s \cdot g^{-1}$) or greater. If the SFC is less than 10 ($10^{-7} \cdot cm^3 \cdot s \cdot g^{-1}$), the liquid permeability is very low. The water absorbing resin, used in the water absorbent core, may not exhibit an excellent liquid acquisition rate per unit time.

The water absorbing resin of the present invention preferably has well-balanced CRC and SFC. Specifically, if the CRC is greater than or equal to 5 g/g and less than 25 g/g, the SFC is preferably 100 ($10^{-7} \cdot cm^3 \cdot s \cdot g^{-1}$) or greater, more preferably 150 ($10^{-7} \cdot cm^3 \cdot s \cdot g^{-1}$) or greater, and the most preferably 300 ($10^{-7} \cdot cm^3 \cdot s \cdot g^{-1}$) or greater. If the CRC is greater than or equal to 25 g/g and less than 30 g/g, the SFC is preferably 30 ($10^{-7} \cdot cm^3 \cdot s \cdot g^{-1}$) or greater, more preferably 70 ($10^{-7} \cdot cm^3 \cdot s \cdot g^{-1}$) or greater, and the most preferably 100 ($10^{-7} \cdot cm^3 \cdot s \cdot g^{-1}$) or greater. If the CRC is more than or equal to 30 g/g and less than 50 g/g, the SFC is preferably 10 ($10^{-7} \cdot cm^3 \cdot s \cdot g^{-1}$) or greater, more preferably 30 ($10^{-7} \cdot cm^3 \cdot s \cdot g^{-1}$) or greater, and the most preferably 50 ($10^{-7} \cdot cm^3 \cdot s \cdot g^{-1}$).

The water absorbing resin of the present invention preferably has a centrifuge retention capacity CRC of 26 g/g to 32 g/g, a mass-average particle diameter D50 of 300 to 500 μm, and such a saline flow conductivity SFC that satisfies a relationship with the centrifuge retention capacity CRC given by the following expression:

$$SFC \geq -20 \times CRC + K,$$

where K is a constant, preferably 670, more preferably 680, most preferably 690.

If a good balance is struck between the CRC and the SFC, the water absorbing resin, used in the water absorbent core, shows a sufficiently high rate of absorption which makes up for a low liquid permeability. On the other hand, if the liquid permeability is high, liquid diffuses in the water absorbing resin, enabling absorption across a wide area, even when the resin shows a low rate of absorption. Thus, the resulting water absorbing resin exhibits an excellent liquid acquisition rate per unit time when used in the water absorbent core.

The water absorbing resin of the present invention has an AAP of 8 g/g or greater, preferably 16 g/g or greater, more preferably 20 g/g or greater, even more preferably 22 g/g or greater, and the most preferably 24 g/g or greater. The maximum AAP, although not limited in any particular manner, is preferably 30 g/g or less. If the AAP is less than 20 g/g, the water absorbing resin, when used in the water absorbent core, may cause lot of liquid seeping, or "rewetting," under pressure.

The extractable polymer content of the water absorbing resin of the present invention is preferably from 0 to 35 mass % inclusive, more preferably from 0 to 25 mass % inclusive, and even more preferably from 0 to 15 mass % inclusive. If the extractable polymer content is in excess of 35 mass %, the gel shows poor strength and liquid permeability. Besides, the water absorbing resin, when used in the water absorbent core, may cause lot of liquid seeping, or "rewetting," under pressure.

The water absorbing resin of the present invention preferably contains extractable polymer content which has a weight-average molecular weight Mw of 150,000 to 500,000 daltons. The weight-average molecular weight Mw is more preferably from 170,000 to 400,000 daltons and most preferably from 180,000 to 300,000 daltons.

The water absorbing resin of the present invention preferably contains extractable polymer content which has an intrinsic viscosity IV of 1.0 to 2.0 dL/g. The intrinsic viscosity IV is more preferably from 1.1 to 1.9 dL/g and most preferably from 1.2 to 1.8 dL/g.

The water absorbing resin of the present invention preferably contains extractable polymer content which has a molecular weight distribution Mw/Mn of 2.0 to 3.0. The molecular weight distribution Mw/Mn is more preferably from 2.1 to 2.8 and most preferably from 2.2 to 2.7.

A water absorbing resin with excellent AAP and SFC is obtainable by setting the weight-average molecular weight Mw, intrinsic viscosity IV, and molecular weight distribution Mw/Mn of the extractable polymer content to the specified ranges. In addition, a water absorbent core is obtainable which has an excellent liquid acquisition rate per unit time when the water absorbing resin is used in a water absorbent core.

The polymerization initiator accounts for 0 to 5 ppm, and more preferably 0 to 2 ppm of the water absorbing resin. It is even more preferably if the initiator is ND (less than detection limit).

The water absorbing resin produces little dust. Dust, if present, is preferably from 0 to 300 ppm inclusive as measured with a Heubach dustmeter (detailed later). So long as this condition is met, the fine particles in the water absorbing resin will not spread in the air, unlikely to raise safety/hygienic issues, during manufacture of the water absorbing resin. Also, the physical properties of the water absorbent core will not be adversely affected.

The water absorbing resin is characterized by a high swelling pressure of gel layer.

The water absorbing resin of the present invention has a mass-average particle diameter D50 of, preferably, 200 to 600 μm and more preferably 300 to 500 μm. If the water absorbing resin has a mass-average particle diameter D50 out of the 200 to 600 μm range, the liquid permeability and diffusibility may fall noticeably, or the absorption rate per unit time may fall by a large value. That water absorbing resin, if used in a diaper for example, may be leaky or otherwise defective.

The particle size distribution of the water absorbing resin of the present invention has a logarithmic standard deviation σζ of preferably 0.20 to 0.50, and more preferably 0.30 to 0.40 inclusive. If the standard deviation is out of the ranges, the liquid permeability may so decrease that the water absorbent core has a very poor liquid acquisition rate per unit time.

Particles that can pass through a sieve of 150-μm mesh and particles with 850 μm or longer diameters preferably constitute 0 to 5 mass % individually of the water absorbing resin of the present invention. The ratio is more preferably from 0 to 3 mass %. The exclusion of water absorbing resin less than 150 μm limits the amount of dust in the resulting water absorbing resin. Thus, the fine particles in the water absorbing resin will not spread in the air, unlikely to raise safety/hygienic issues, during manufacture of the water absorbing resin. Also, the physical properties of the resultant water absorbing resin will not be adversely affected. If the ratio is in excess of 5 mass %, dust can occur during manufacture of the water absorbing resin, possibly raising safety/hygienic issues or degrading the physical properties of the water absorbent core, to name a few problems.

The water absorbing resin of the present invention has an absorption rate per unit time (FSR) of 0.2 g/g/s or greater, preferably 0.3 g/g/s or greater, more preferably 0.5 g/g/s or greater, even more preferably 0.7 g/g/s or greater, for physiological saline diluted 20-fold. The maximum FSR, although not limited in any particular manner, is preferably 10 g/g/s or less, and more preferably 5 g/g/s or less. If the absorption rate per unit time (FSR) is less than 0.2 g/g/s, that water absorbing resin, used in a diaper for example, may not absorb a sufficient amount of urine, allowing it to leak.

The water absorbing resin of the present invention contains a polyvalent metal salt at least either on the surface or near the surface in a ratio of preferably 0.001 mass % to 5 mass % inclusive, and more preferably 0.01 mass % to 1 mass % inclusive, relative to the water absorbing resin. Owing to the inclusion of a polyvalent metal salt (preferably, a water-soluble trivalent metal salt), the water absorbing resin shows improved saline flow conductivity SFC while substantially preserving its absorbency under the pressure of 4.83 kPa AAP and fixed height absorbency FHA. Preferable concrete examples of the polyvalent metal salt are listed earlier.

The water absorbing resin of the present invention preferably contains the α-hydroxy carboxylic acid (salt). The ratio of the α-hydroxy carboxylic acid (salt) contained in the water absorbing resin to the water absorbing resin is from 0.1 to 10 mass %, preferably from 0.1 to 5 mass %, more preferably 0.15 to 3 mass %, and the most preferably 0.2 to 3 mass %. If a particulate water absorbing resin contains the α-hydroxy carboxylic acid (salt) in a ratio out of these ranges, it becomes difficult to strike a good balance between water absorption properties (especially, SFC) and coloring prevention.

Water Absorbent Core

The water absorbent core of the present embodiment contains the water absorbing resin described in the foregoing. The water absorbent core, when used in combination with an appropriate material, is suited for use as an absorbent layer in sanitary/hygienic materials, for example. The following will describe the water absorbent core.

The water absorbent core is a molded composition made of the water absorbing resin and other materials. The core is used in disposable diapers, sanitary napkins, incontinent pads, medical pads, and like sanitary/hygienic materials to absorb blood, body fluids, urine, etc. An example of the other materials used in combination with the water absorbing resin is cellulose fiber. Concrete examples of cellulose fiber include mechanical pulp made from wood; wood pulp fibers, such as chemical pulp, semi-chemical pulp, and soluble pulp; and artificial cellulose fibers, such as rayon and acetate. Preferred cellulose fiber is the wood pulp fibers. The cellulose fiber may partially contain nylon, polyester, or another synthetic fiber. When the water absorbing resin of the present embodiment is used as part of the water absorbent core, the mass of the water absorbing resin contained in the water absorbent core is preferably 20 mass % or more, more preferably 30 mass % or more, even more preferably 40 mass % or more, still preferably 60 wt % or more. If the mass of the water absorbing resin of the present invention contained in the water absorbent core is less than 20 mass %, sufficient effects may not be accomplished.

A publicly known, suitable method for producing a water absorbent core may be selected to produce the water absorbent core from the water absorbing resin of the present embodiment and the cellulose fiber. For example, the water absorbing resin may be sprayed onto sheets or mats made of the cellulose fiber and sandwiching more of the resin between them if necessary. Alternatively, the cellulose fiber may be uniformly blended with the water absorbing resin. A preferred method is to dry mix the cellulose fiber with the water absorbing resin and compress the mixture. This method is highly capable of restraining the water absorbing resin from falling off the cellulose fiber. The compression is preferably carried out on heating at, for example, 50° C. to 200° C. inclusive.

The water absorbing resin of the present embodiment, when used in the water absorbent core, exhibits excellent physical properties; the resultant water absorbent core is of very excellent quality in that it can quickly absorb liquid, leaving only a little liquid on its surface.

The water absorbing resin of the present embodiment has an excellent water absorption property and hence is applicable to water absorbing/retaining agents for various purposes: for example, water absorbing/retaining agents for absorbent articles, such as disposable diapers, sanitary napkins, incontinent pads, and medical pads; agriculture/horticulture water retaining agents, such as bog moss replacements, soil conditioners, water retaining agents, and agricultural chemical enhancers; water retaining agents for construction purposes, such as dew inhibitors for interior wall materials and cement additives; release controlling agents; cold insulators; disposable pocket stoves; sludge coagulating agent; food freshness retaining agents; ion exchange column materials; sludge/oil dehydrates; desiccants; and humidity conditioning agents. In addition, the water absorbing resin of the present embodiment is especially suitable for use in disposable diapers, sanitary napkins, and like sanitary/hygienic materials for absorbing feces, urine, or blood.

Where the water absorbent core is used in sanitary/hygienic materials, such as disposable diapers, sanitary napkins, incontinent pads, and medical pads, it is preferable if the core is placed between (a) a top sheet, permeable to liquid, provided next to the body of the user and (b) a back sheet, impermeable to liquid, provided next to the clothes of the user away from the body of the user. The water absorbent core may be multi-layered (two or more layers). Further, the core may be used with a pulp layer as an example.

EXAMPLES

The following will more specifically describe the present invention by way of examples. The examples are by no means limiting the present invention. Throughout the following, "mass parts" may be written simply as "parts" and "liter" as "L" only for the sake of convenience. Also, "mass %" may be written as "wt %."

The performance of the water absorbing resin was measured by the following methods. Unless otherwise specified, all the measurements were conducted at room temperature (20 to 25° C.) and 50 RH % humidity.

In the cases of the water absorbing resin being used in an end product, such as a sanitary/hygienic material, the water absorbing resin had already absorbed moisture. The water absorbing resin was therefore separated appropriately from the end product and dried under reduced pressure and at low temperature (for example, under 1 mmHg or lower and at 60° C. for 12 hours) before measurements were made. All the water absorbing resins used in the examples and the comparative examples contained 94 mass % or more solid content.

Centrifuge Retention Capacity (CRC)

Centrifuge retention capacity, or CRC, is absorption capacity for 0.90 mass % saline under no load over 30 minutes. CRC may be referred to as "absorption capacity under no load."

0.200 g of the water absorbing resin was placed evenly in a bag (85 mm×60 mm) of non-woven fabric ("Heatron Paper" GSP-22, manufactured by Nangoku Pulp Kogyo Co., Ltd.). After heat sealing, the bag was immersed in a largely excessive amount (typically about 500 mL) of 0.90 mass % saline (aqueous solution of sodium chloride) at room temperature. After 30 minutes, the bag was taken out of the saline and centrifuged for 3 minutes in a centrifugal separator ("Centrifuge H-122," manufactured by Kokusan Co., Ltd.) under centrifugal force described in edana ABSORBENCY II 441.1-99 (250 G). The mass, $W1$ (g), of the bag was then measured. The same process was carried out using no water absorbing resin, and the mass, $W0$ (g), of the bag was measured. The centrifuge retention capacity CRC was calculated in grams per gram from $W1$, $W0$ as given by the following equations:

$$\text{Centrifuge Retention Capacity CRC (g/g)}=(W1\text{ (g)}-W0\text{ (g)})/(\text{Mass (g) of Water Absorbing Resin})-1$$

Absorbency Against Pressure of 4.83 kPa (AAP)

Figure 3:
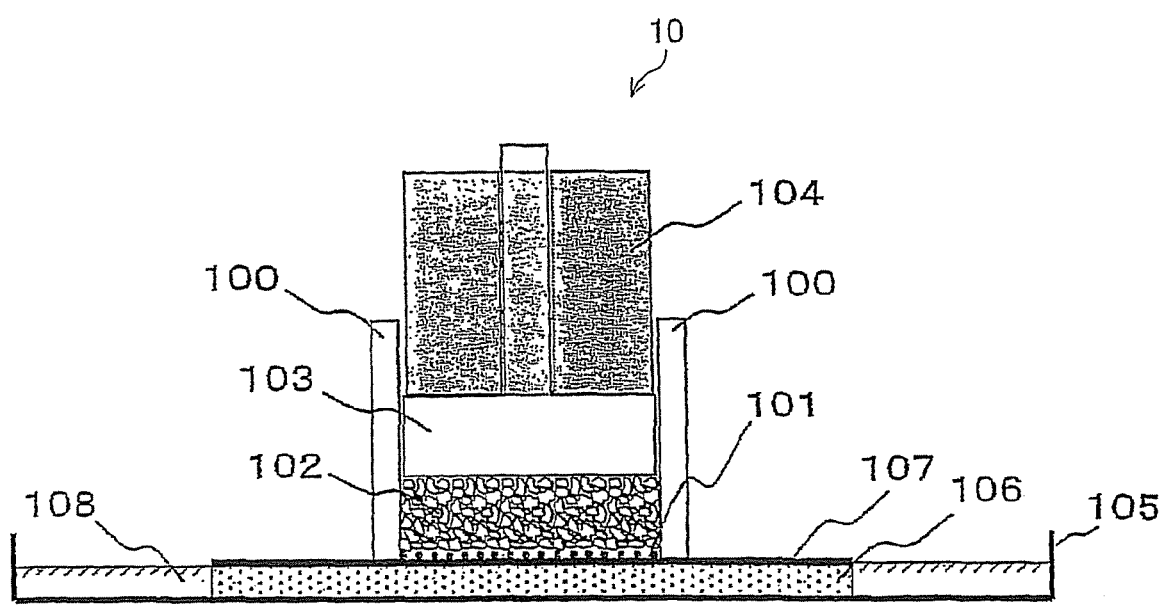
FIG. 3 is a schematic illustration of a measurement apparatus used to measure AAP.

Absorbency against pressure, or AAP, is absorption capacity for 0.90 mass % saline under 4.83 kPa over 60 minutes. AAP may be referred to as absorption capacity under 4.83 kPa. FIG. 3 is a cross-sectional view of an AAP measurement apparatus 10.

In the measurement apparatus 10 shown in FIG. 3, a 400-mesh stainless steel net 101 (mesh size 38 µm) was fused to the bottom of a plastic supporter cylinder 100 that had an internal diameter of 60 mm. 0.900 g of the water absorbing resin was sprayed evenly on the net 101 at room temperature (from 20° C. to 25° C. inclusive) and 50 RH % humidity. A piston 103 and a weight 104 were placed in this order on the water absorbing resin, or the test sample 102. The piston 103 and weight 104 had an external diameter slightly less than 60 mm so that there occurred no gap between them and the supporter cylinder 100 and their up and down motion was not disturbed. The piston 103 and weight 104 were adjusted so that they could apply a 4.83 kPa (0.7 psi) load evenly. The mass, $Wa$ (g), of the entire measurement apparatus 10 was measured.

A glass filter 106 measuring 90 mm in diameter (manufactured by Sogo Laboratory Glass Works Co., Ltd.; pore diameter 100 to 120 µm) was placed inside a petri dish 105 measuring 150 mm in diameter. 0.90 mass % saline 108 (from 20° C. to 25° C. inclusive) was poured until it sit level with the top face of the glass filter 106. A paper filter 107 measuring 90 mm in diameter ("JIS P 3801, No. 2," Advantec Toyo Kaisha, Ltd.; thickness 0.26 mm, retainable particle diameter 5 µm) was placed on the filter 106 so that the surface of the filter 107 could be all wet. Excess solution was removed.

The whole measurement apparatus 10 was placed on the wet paper filter so that it could absorb the solution under load. After 1 hour, the whole measurement apparatus 10 was lifted, and its mass $Wb$ (g) was measured. The absorbency under 4.83 kPa (AAP) was calculated in grams per gram from $Wa$, $Wb$ as given by the following equation:

$$\text{Absorbency under 4.83 kPa (AAP)}=(Wb\text{ (g)}-Wa\text{ (g)})/(\text{Mass of Water Absorbing Resin (0.900 g)})$$

Saline Flow Conductivity (SFC)

Saline flow conductivity, or SFC, is a value indicating liquid permeability of the water absorbing resin when it has swollen. The greater the SFC, the higher liquid permeability the water absorbing resin has. SFC tests were conducted in the examples as described in the Specification of U.S. Pat. No. 5,849,405. FIG. 1 is a schematic illustration of an SFC measurement apparatus 30.

In the measurement apparatus 30 shown in FIG. 1, a glass tube 32 was inserted into a tank 31. The lower end of the glass tube 32 was arranged so that 0.69 mass % saline 33 could be maintained 5 cm above the bottom of a gel 44 in a cell 41. The 0.69 mass % saline 33 in the tank 31 was fed to a cell 41 via an "L" tube 34 which has a valve 35. Under the cell 41 was provided a collector 48 which collected the solution that had passed through the cell 41. The collector 48 was placed on a balance 49. The cell 41 had an internal diameter of 6 cm and was provided with a No. 400 stainless steel net (mesh 38 µm) 42 on the bottom. The piston 46 had, on its lower part, holes 47 through which the solution could properly pass. Also, the piston 46 had a high permeability glass filter 45 attached to its bottom so that the water absorbing resin, or their swollen gel could not enter the holes 47. The cell 41 was placed on a base. The face of the base at which it contacted the cell 41 was disposed on a stainless steel net 43 which did not disturb the passing solution.

Artificial urine (1) used here was a mixture of 0.25 g calcium chloride dihydrate, 2.0 g potassium chloride, 0.50 g magnesium chloride hexahydrate, 2.0 g sodium sulfate, 0.85 g ammonium dihydrogenphosphate, 0.15 g diammonium hydrogenphosphate, and 994.25 g pure water.

The water absorbing resin (0.900 g) placed evenly in the container 40 was let to swell, using the measurement apparatus 30 shown in FIG. 1, in artificial urine (1) under a load of 2.07 kPa (0.3 psi) for 60 minutes to prepare the gel 44. Thereafter, the height of the layer of the gel 44 was recorded. Next, the 0.69 mass % saline 33 was passed through the swollen gel layer from the tank 31 under a load of 2.07 kPa (0.3 psi) at a constant hydrostatic pressure. The SFC test was conducted at room temperature (from 20° C. to 25° C. inclusive). The amount of liquid having passed through the gel layer was recorded using a computer and a scale as a function of time at 20 second intervals for 10 minutes. The flow rate $Fs(T)$ at which the solution passed through the swollen gel 44 (primarily between the gel's particles) was determined in units of grams per second by dividing an increase in mass (g) by an increase in time (s). Flow rates were calculated only from the data obtained in the 10 minute period starting at time Ts at which a constant hydrostatic pressure and a stable flow rate were achieved. Fs(T=0), or the first flow rate at which the solution passed through the gel layer, was calculated from the flow rates obtained in the 10 minute period starting at Ts. Fs(T=0) was obtained by extrapolating, for T=0, the result of least square approximation of Fs(T) vs. time.

$$\text{Saline Flow Conductivity } (SFC) = (Fs(T=0) \times L0)/(\rho \times A \times \Delta P)$$
$$= (Fs(T=0) \times L0)/139506$$

where Fs(T=0) was the flow rate in grams per second; L0 was the height of the gel layer in centimeters; ρ was the density of the NaCl solution (=1.003 g/cm$^3$); A was the area of the top face of the gel layer in the cell 31 (=28.27 cm$^2$); and ΔP was the hydrostatic pressure exerted on the gel layer (=4920 dyne/cm$^2$). The SFC values were given in units of $10^{-7} \cdot \text{cm}^3 \cdot \text{s} \cdot \text{g}^{-1}$.

Fixed Height Absorbency (FHA)

Fixed Height Absorbency, or FHA, was measured in accordance with the method described in U.S. Published Patent Application 2005/0003191A1. The height upon measurement was set to 20 cm in the present invention.

Mass-Average Particle Diameter D50 and Logarithmic Standard Deviation, σζ, of Particle Size Distribution These two parameters were measured based on the tests for the mass-average particle diameter, or D50, and the logarithmic standard deviation, σζ, of a particle size distribution described in International Application Published under PCT WO2004/69915.

Liquid Distribution Velocity (LDV)

Liquid distribution velocity, or LDV, was measured using a wicking index measurement apparatus described in Japanese Unexamined Patent Publication 5-200068/1993 (Tokukaihei 5-200068; equivalent to EP 532002). The trough sheet was prepared by SUS304, stainless steel, grade 2B finish for measurement.

First, 1.00 g±0.005 g of the water absorbing resin was sprayed evenly from the 0 to 20 cm marks in trough grooves on a trough sheet disposed at an angle of 20° C. The water absorbing resin was then more evenly spread using a spatula.

The liquid to be wicked away was 0.9 wt % saline (aqueous solution of sodium chloride) to which "Blue No. 1 for Food Testing" (available from Tokyo Chemical Industry Co., Ltd.) was added in a ratio of 0.01 g for every 1 L of the saline for coloring.

Adjustment was made so that the liquid surface in a liquid storage vessel was 0.5 cm above the lowest point in the trough. After that, measurement of a liquid wicking time (WT) was started right when the stainless steel screen mesh (400-mesh) contacted the liquid. The liquid wicking time (WT) was the time in seconds it took for the liquid to be wicked up to the 10 cm mark. The velocity at which the liquid in the liquid storage vessel and the stainless steel screen mesh were immersed down to 0.5 cm above the lowest point in the trough was from 1.35 to 1.40 mm/s in the direction perpendicular to the liquid surface. The liquid distribution velocity (LDV) was calculated from the following equation:

LDV (mm/s)=100 (mm)/WT (s)

Ratio of Particles of Sizes which Pass through 150-μm Meshes of Sieve

The same classification process was performed as in the measurement of the mass-average particle diameter D50 and the logarithmic standard deviation, σζ, of a particle size distribution. The ratio in mass % of the particles of sizes that could pass through a sieve with 150-μm meshes was calculated from the amount of the particles that had passed through that sieve with the 150-μm meshes.

Extractable Polymer Content (Water-Soluble Components)

184.3 g of 0.90 mass % saline was prepared in a lidded plastic container (capacity 250 mL). 1.00 g of the water absorbing resin was added to the aqueous solution. A stirrer was rotated for 16 hours to extract extractable polymer content of the resin by stirring the mixture. The liquid extract was filtered through a paper filter ("JIS P 3801, No. 2," Advantec Toyo Kaisha, Ltd.: thickness 0.26 mm, retainable particle diameter 5 μm). 50.0 g of the obtained filtrate was set aside for measurement as a sample solution.

First, a 0.1 N aqueous solution of NaOH was added to the 0.90 mass % saline alone, to pH 10. Then, a 0.1 N aqueous solution of HCl was added to pH 2.7 to determine a blank titer ([bNaOH] mL, [bHCl] mL).

The same titration process was performed on the sample solution to determine a titer ([NaOH] mL, [HCl] mL).

In the case of a water absorbing resin made of known amounts of an acrylic acid and its sodium salt as an example, the extractable polymer content of the water absorbing resin could be calculated according to the following equation from the weight-average molecular weight Mw of the monomer and the titer determined by the above-mentioned process. If the water absorbing resin was made of unknown amounts of an acrylic acid and its sodium salt, the weight-average molecular weight Mw of the monomer was calculated based on the neutralization ratio determined by the titration.

$$\text{Extractable polymer content (mass \%)} =$$
$$0.1 \times \text{Weight-Average Molecular Weight } Mw \times$$
$$184.3 \times 100 \times ([\text{HCl}] - [b\text{HCl}])/1000/1.0/50.0$$

$$\text{Neutralization Ratio (mol \%)} = (1 - ([\text{NaOH}] - [b\text{NaOH}])/([\text{HCl}] - [b\text{HCl}])) \times 100$$

Amount of Dust (Dust Related Properties)

The increase in mass of the dust absorbed and collected by a glass fiber filter over a predetermined period of time under the conditions detailed below was measured as the amount of dust in the water absorbing resin. The measurement was carried out on a Heubach Dustmeter manufactured by Heubach Engineering GmbH in Germany operating in measuring mode I. The atmospheric conditions during the measurement were 25° C. (±2° C.) temperature, 20 to 40% relative humidity, and normal pressure. Specific procedures were as follows.

(1) 100.00 g of a sample (water absorbing resin) was placed in a rotation drum 200.

(2) The mass of the glass fiber filter 50 mm in diameter (retainable particle diameter 0.5 μm (JIS P3801)) was measured with 0.00001 gram accuracy ("Da" grams). The filter was prepared by fabricating, for example, Advantec's glass fiber, GC-90, or any equivalent to the 50 mm diameter.

(3) A large-scale particle separator 201 was attached to the rotation drum 200. A filter enclosure 202 loaded with a glass fiber filter 204 was also attached.

(4) Conditions were set as follows on the control section 203 of the dustmeter. Measurement was made.

Rotation Rate of Drum=30 R/min
Volume of Absorbed Air=20 L/min
Time (Measurement Period)=30 minutes (5) After the predetermined period, the mass of the glass fiber filter 204 was measured with 0.00001 gram accuracy ("Db").

The amount of dust was given by:

Amount of Dust (ppm)=$(Db-Da)/100.00 \times 1{,}000{,}000$

Paint Shaker Test

In a paint shaker test (PS), a glass container 6 cm in diameter and 11 cm in height was charged with 10 g of glass beads each 6 mm in diameter and 30 g of a water absorbing resin and loaded in a paint shaker (No. 488, Toyo Seiki Seisakusho Co., Ltd.) for shaking at 800 cycles per minute (CPM). See Japanese Unexamined Patent Publication 9-235378/1997 (Tokukaihei 9-235378) for details of the device.

Tests in which the shake time was set to 30 minutes and 10 minutes were designated paint shaker test 1 and paint shaker test 2 respectively.

After infiltration, the glass beads were removed using a JIS Standard sieve (mesh 2 mm), leaving behind damaged water absorbing resin.

Solid Content of Water Absorbing Resin

The value indicates the ratio in the water absorbing resin of components that do not volatilize at 180° C. The solid content is related with the water content as follows:

Solid Content (mass %)=100−Water Content (mass %)

The solid content was measured as in the following.

About 1 g of the water absorbing resin (actual mass $W_1$) was measured and placed in an aluminum cup (mass $W_0$) about 5 cm in bottom diameter. The cup was then placed in a windless drier at 180° C. to sit there for 3 hours for drying. The combined mass, $W_2$, of the aluminum cup and the water absorbing resin after the drying was measured. The solid content was determined by the following equation:

Solid Content (mass %)=$((W_2-W_0)/W_1) \times 100$

Solid Content of Water-Containing Gel

The solid content of a water-containing gel was measured by the same method as with the solid content of a water absorbing resin, except that the water-containing gel weighed about 5 g and also that the cup sat in the drier for 8 hours for drying.

Intrinsic Viscosity IV and Weight-Average Molecular Weight Mw at Log(Molecular Weight)=6.10

Preparation of Samples

A polypropylene test tube (internal diameter 1.8 cm, length 15 to 18 cm) was charged with 50 mg of the water absorbing resin and 10 g of a 0.1 mol/L aqueous solution of sodium hydroxide (for use in capacity analysis, manufactured by Wako Pure Chemical Ind.) and closed with a polypropylene seal. The test tube was shielded from light and left to sit at 80° C. for 3 weeks. The solution thus obtained was diluted 6-fold with the solvent detailed below and passed through a filter (GL Chromatodisk, Aqueous 25A, manufactured by GL Sciences Inc., pore diameter 0.2 μm). Measurement was done on the solution under the following conditions.

Conditions for Measurement

The measurement was carried out using a TDA302 (Registered Trademark) manufactured by Viscotek Corporation. The apparatus was configured from a size exclusion chromatography device, a refractive index detector, an optical scatter detector, and a capillary viscosity meter. Details of the apparatus and its settings were as follows:

Pump Autosampler: GPCmax from Viscotek Corporation.
Guard Column: SHODEX GF-7B
Column: Two TOSOH GMPWXLs Connected In Series
Detector: TDA302 from Viscotek Corporation (system temperature maintained at 30° C.)
Solvent: Aqueous Solution of 60 mM Sodium Dihydrogenphosphate Dihydrate and 20 mM Disodium Hydrogenphosphate Dodecahydrate
Flow Rate: 0.5 mL/min
injection: 100 μL The apparatus was calibrated using polyoxyethylene glycol (weight-average molecular weight Mw=22,396, differential refractive index dn/dc=0.132, refractive index of solvent=1.33) as a reference sample.

In the case of the water absorbing resin being obtained by polymerization of a monomer containing 99 mol % or more acrylic acid and/or its salt, the measurement was carried out presuming that the differential refractive index dn/dc of the target polymer for analysis was 0.12. In the case of the water absorbing resin being obtained by copolymerizing a monomer more than 1% of which is not an acrylic acid and/or its salt, the differential refractive index (dn/dc) may be measured in the foregoing solvent that is unique to that polymer, and its value be used.

Data on the refractive index, intensity of scattered light, and viscosity were collected and analyzed using software, Viscotek Corporation OmniSEC 3.1 (Registered Trademark). The weight-average molecular weight Mw was calculated from the data obtained from the refractive index and the intensity of scattered light. In addition, from the refractive index, the intensity of scattered light, and the data obtained from the viscosity meter, Mark-Houwink-Sakurada plotting was carried out with the X axis indicating Log(Mw) (molecular weight) and the Y axis indicating Log(IV) (intrinsic viscosity). The value of Log(IV) at Log(Mw)=6.1 was read from the line drawn, and the intrinsic viscosity IV was calculated from that value. The intrinsic viscosity (IV) has the same meaning with the limiting viscosity (IV) throughout the specification.

Thermally Decomposing Radical Initiator Content Index

The thermally decomposing radical initiator content index is a numeric value obtained from the mole ratio of a thermally decomposing radical initiator and a the number of monomer units in a polymer in a water-containing gel. The index is given by the following equation:

Thermally Decomposing Radical Initiator Content index=$(Ci/Mi)/(Cm/Mm) \times 10^5$ where:

Ci is the quantity in mass % of a thermally decomposing radical initiator extracted by stirring a water-containing gel in a 5% aqueous solution of sodium chloride for 1 hour immediately prior to the drying step;

Mi is the mole-average molecular weight in mol/g of the extracted thermally decomposing radical initiator;

Cm is the solid content in mass % of the water-containing gel obtained by drying the water-containing gel at 180° C. for 8 hours; and Mm is the mole-average molecular weight in mol/g of a polymerized monomer.

Measurement of Quantity, Ci (Mass %), of Thermally Decomposing Radical Initiator for Water-Containing Gel A lidded polypropylene container (capacity 260 mL) was charged with 10 g of the water-containing gel immediately prior to the drying step and 170 g of a 5% aqueous solution of sodium chloride. If the gel has swollen and cannot be stirred, the concentration of the salt or the amount of the aqueous solution is adjusted properly. The solution was then stirred while the container was kept shielded from light and at room temperature. After 1 hour, the solution was removed from the container and passed through a filter (GL Chromatodisk, Aqueous 25A, manufactured by GL Sciences Inc. pore diameter 0.45 μm). 4.00 g of the filtered solution was put in a glass sample vial with a screw cap (capacity 50 mL, diameter 35 Mm, height about 80 mm), to which 6.00 g of a 5% aqueous solution of sodium chloride was added. Then, 1.00 g of a 44 mass % aqueous solution of potassium iodide was added immediately, and the mixture was stirred while the container was kept shielded from light and at room temperature. After 1 hour, the solution was transferred to a 1-cm plastic cell. Absorption of 350 nm light was measured with a spectrophotometer (Hitachi Ratio Beam Spectrophotometer U-1100), taking the absorption of light by pure water to be 0. The quantity, Ci, of the thermally decomposing radical initiator in the water-containing gel was calculated in mass % from the light absorption value thus obtained.

An inspection line was drawn from light absorption measurements obtained by the same process as above from 5% aqueous solutions of sodium chloride containing the thermally decomposing radical initiator in the respective ratios of 0.0005, 0.0010, 0.0015, and 0.0020 mass %. The quantity, Ci (mass %), of the thermally decomposing radical initiator in the water-containing gel was calculated from the inspection line and the light absorption.

Provided that the inspection line is given by a mathematically expression:

Quantity of Thermally Decomposing Radical Initiator (mass %)= $a \times$(Absorption of Light)$+b$,
where $a$ and $b$ are constants, the quantity, Ci (mass %), of the thermally decomposing radical initiator in the water-containing gel is given by the following equation:

Quantity, Ci (mass %), of Thermally Decomposing Radical Initiator=$(a \times$(Absorption of Light)$+b) \times ((170+10)/10) \times ((6+4)/4)$ Solid Content, Cm, in Water-Containing Gel (Mass %)

The solid content, Cm, in the water-containing gel was measured by the method described above.
Weight-Average Molecular Weight Mw, Number-Average Molecular Weight Mn, and Molecular Weight Distribution Mw/Mn after Treatment of Set 2 of Hydrolysis Conditions
Preparation of Samples A polypropylene test tube (internal diameter 1.8 cm, length 15 to 18 cm) was charged with 20 mg of the water absorbing resin and 10 g of a 0.1 mol/L aqueous solution of sodium hydroxide (for use in capacity analysis, manufactured by Wako Pure Chemical Ind.) and closed with a polypropylene seal. The test tube was shielded from light and left to set at 80° C. for 3 weeks. After the 3 weeks, the water absorbing resin was hydrolyzed and in a solution state. After the hydrolysis, insoluble content accounted for usually 50 mass % or less, preferably 10 mass % or less, more preferably 0 mass %, of the water absorbing resin.

The solution thus obtained was diluted 4-fold with the solvent detailed below and passed through a filter (GL Chromatodisk, Aqueous 25A, manufactured by GL Sciences Inc., pore diameter 0.2 μm). Measurement was done on the solution under the following conditions.
Conditions for GPC Measurement The measurement was carried out using a TDA302 (Registered Trademark) manufactured by Viscotek Corporation. The apparatus was configured from a size exclusion chromatography device, a refractive index detector, an light scattering detector, and a capillary viscosity meter.

Details of the apparatus and its settings were as follows:
Pump Autosampler: GPCmax from Viscotek Corporation
Guard Column: OHpak SB-G (manufactured by Showa Denko K.K.)
Column: Two OHpak SB-806 MHQs (manufactured by Showa Denko K.K.) Connected In Series
Detector: TDA302 from Viscotek Corporation (system temperature maintained at 30° C.)
Solvent: Aqueous Solution (pH6.35 to 6.38) of 60 mM Sodium Dihydrogenphosphate Dihydrate, 20 mM Disodium Hydrogenphosphate Dodecahydrate, and 400 ppm Sodium Azide
Flow Rate: 0.5 mL/min
Injection: 100 μL Impurities were removed sufficiently from the pure water used in the measurement. Before the measurement, a sufficient amount of solvent was passed through the device so as to gat a stable base line for detection values. Especially, the measurement was carried out while the light scattering detector shows no noise peaks.

The apparatus was calibrated using polyoxyethylene glycol (weight-average molecular weight Mw=22,396, molecular weight distribution Mw/Mn=1.0, differential refractive index dn/dc=0.132, refractive index of solvent=1.33) as a reference sample.

In the case of the water absorbing resin being obtained by polymerization of a monomer containing 99 mol % or more acrylic acid and/or its salt, the measurement was carried out presuming that the differential refractive index dn/dc of the target polymer for analysis was 0.12 and also that the refractive index of the solvent was 1.33. In the case of the water absorbing resin being obtained by copolymerizing a monomer more than 1% of which is not an acrylic acid and/or its salt, the differential refractive index (dn/dc) may be measured in the foregoing solvent that is unique to that polymer, and its value be used.

A chart drawn from the measurement was checked. If the peak obtained from the measurement of the intensity of scattered light contains a lot of noise, the measurement was carried out again.

Data on the refractive index, intensity of scattered light, and viscosity were collected and analyzed using software, Viscotek Corporation OmniSEC 3.1 (Registered Trademark). The weight-average molecular weight Mw, number-average molecular weight Mn, molecular weight distribution Mw/Mn, and intrinsic viscosity IV were calculated from the data obtained from the refractive index RI and the intensity of scattered light LALS (angle 7°) as well as data from a viscosity meter (DP).
Weight-Average Molecular Weight Mw, Number-Average Molecular Weight Mn, and Molecular Weight Distribution Mw/Mn of Extractable Polymer Content
Preparation of Samples The solutions obtained as under the heading "Extractable polymer content (Water-soluble Components)" was used. If the sample concentration was too high, the sample was diluted with a suitable GPC solution so that the polymer content concentration could be about 0.5 mg/mL.
Conditions for Measurement Measurement was carried out under the same conditions as the GPC measurement.

Example 1

436.4 g of an acrylic acid, 4617.9 g of a 37 mass % aqueous solution of sodium acrylate, 373.8 g of pure water, and 11.40 g of polyethylene glycol diacrylate (weight-average molecular weight Mw 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 36.33 g of a 10 mass % aqueous solution of sodium persulfate and 24.22 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. After the polymerization started, it took not longer than 15 minutes to reach a maximum temperature. The resulting water-containing gel (water-containing gel-like crosslinked polymer) had been comminuted to a diameter of about 5 mm or less.

The water-containing gel contained 0.0547 mass % thermally decomposing radical initiator (=Ci mass %) and 40.9 mass % solid content (=Cm mass %). The thermally decomposing radical initiator content index was 49.7. These results are shown in Table 1.

The comminuted water-containing gel-like crosslinked polymer was spread on a 50-mesh metal net and dried in hot wind at 180° C. for 45 minutes. The dried substance was pulverized in a roll mill and subjected to a classification using a JIS-standard sieve having a mesh opening size of 710 μm. Those particles which had passed through that sieve were then passed through a JIS-standard sieve having a mesh opening size of 175 μm for further classification. The fine particles having passed through the sieve were removed to obtain water absorbing resin (1) which had an irregularly pulverized shape. Resin (1) had a mass-average particle diameter D50 of 341 μm. The logarithmic standard deviation, σζ, of the particle size distribution of resin (1) was 0.33. Water absorbing resin (1) had a centrifuge retention capacity CRC of 34.4 g/g and contained 7.6 mass % extractable polymer content. The particles of such sizes that they could pass through a sieve having a mesh opening size of 150 μm accounted for 1.7 mass % of resin (1). Table 3 shows measurements by the aforementioned method of the intrinsic viscosity IV and the weight-average molecular weight Mw for water absorbing resin (1) at such a weight-average molecular weight Mw that Log(Mw)= 6.10.

100 mass parts of obtained water absorbing resin (1) was evenly mixed with a surface crosslinking agent that was a mixed solution of 0.38 mass part 1,4-butanediol, 0.63 mass part propylene glycol, and 2.74 mass part pure water. After the mixing, the mixture was heat treated at 212° C. Sample mixtures were prepared with different heating times: 25 minutes, 30 minutes, and 35 minutes. Thereafter, the resulting particle samples were disintegrated until they could pass through a JIS-standard sieve having a mesh opening size of 710 μm. Next, the disintegrated particle samples were subjected to paint shaker test 1, to obtain surface-crosslinked water absorbing resins: the one heated for 25 minutes was designated water absorbing resin (1-25), the one heated for 30 minutes water absorbing resin (1-30), and the one heated for 35 minutes water absorbing resin (1-35). Table 3 shows measurements by the aforementioned method of the intrinsic viscosity IV and the weight-average molecular weight Mw for water absorbing resins (1-30) and (1-35) at such a weight-average molecular weight Mw that Log(Mw)=6.10.

A mixed solution of 0.40 mass parts of a 27.5 mass % aqueous solution of aluminum sulfate (equivalent to 8 mass % aluminum oxide), 0.134 mass parts of a 60 mass % aqueous solution of sodium lactate, and 0.002 mass part propylene glycol was added to the surface-crosslinked water absorbing resins (1-25), (1-30), and (1-35) each 100 mass parts. After the addition, the mixtures were dried in a windless environment for 1 hour at 60° C. Following the drying, these particle samples were disintegrated until they could pass through a JIS-standard sieve having a mesh opening size of 710 μm. Next, the disintegrated particle samples were subjected to paint shaker test 2, to obtain water absorbing resins: the one obtained from water absorbing resin (1-25) was designated water absorbing resin (1-25A), the one obtained from water absorbing resin (1-30) water absorbing resin (1-30A), and the one obtained from water absorbing resin (1-35) water absorbing resin (1-35A).

Table 2 shows measurements of the CRC, AAP, SFC, D50, and ratio of particles of such sizes that they could pass through a sieve having a mesh opening size of 150 μm for water absorbing resins (1-25A), (1-30A), and (1-35A).

Example 2

436.4 g of an acrylic acid, 4617.9 g of a 37 mass % aqueous solution of sodium acrylate, 377.5 g of pure water, and 10.13 g of polyethylene glycol diacrylate (weight-average molecular weight Mw 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 33.91 g of a 10 mass % aqueous solution of sodium persulfate and 24.22 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. After the polymerization started, it took not longer than 15 minutes to reach a maximum temperature. The resulting water-containing gel (water-containing gel-like crosslinked polymer) had been comminuted to a diameter of about 5 mm or less.

The water-containing gel contained 0.0504 mass % thermally decomposing radical initiator (=Ci mass %) and 41.2 mass % solid content (=Cm mass %). The thermally decomposing radical initiator content index was 45.5. These results are shown in Table 1.

The comminuted water-containing gel-like crosslinked polymer was spread on a 50-mesh metal net and dried in hot wind at 180° C. for 45 minutes. The dried substance was pulverized in a roll mill and subjected to a classification using a JIS-standard sieve having a mesh opening size of 710 μm. Those particles which had passed through that sieve were then passed through a JIS-standard sieve having a mesh opening size of 175 μm for further classification. The fine particles having passed through the sieve were removed to obtain water absorbing resin (2) which had an irregularly pulverized shape. Resin (2) had a mass-average particle diameter D50 of 340 μm. The logarithmic standard deviation, σζ, of the particle size distribution of resin (2) was 0.33. Water absorbing resin (2) had a centrifuge retention capacity CRC of 34.7 g/g and contained 7.5 mass % extractable polymer content. The particles of such sizes that they could pass through a sieve having a mesh opening size of 150 μm accounted for 1.6 mass % of resin (2).

100 mass parts of obtained water absorbing resin (2) was evenly mixed with a surface crosslinking agent that was a mixed solution of 0.38 mass part 1,4-butanediol, 0.63 mass part propylene glycol, 3.39 mass part pure water, and 0.1 mass part sodium persulfate. After the mixing, the mixture was heat treated at 212° C. Sample mixtures were prepared with different heating times: 35 minutes, 40 minutes, and 45 minutes. Thereafter, the resulting particle samples were disintegrated until they could pass through a JIS-standard sieve having a mesh opening size of 710 μm. Next, the disintegrated particle samples were subjected to paint shaker test 1, to obtain surface-crosslinked water absorbing resins: the one heated for 35 minutes was designated water absorbing resin (2-35), the one heated for 40 minutes water absorbing resin (2-40), and the one heated for 45 minutes water absorbing resin (2-45).

A mixed solution of 0.40 mass parts of a 27.5 mass % aqueous solution of aluminum sulfate (equivalent to 8 mass % aluminum oxide), 0.134 mass parts of a 60 mass % aqueous solution of sodium lactate, and 0.002 mass part propylene glycol was added to the surface-crosslinked water absorbing resins (2-35), (2-40), and (2-45) each 100 mass parts. After the addition, the mixtures were dried in a windless environment for 1 hour at 60° C. Following the drying, these particle samples were disintegrated until they could pass through a JIS-standard sieve having a mesh opening size of 710 μm. Next, the disintegrated particle samples were subjected to paint shaker test 2, to obtain water absorbing resins: the one obtained from water absorbing resin (2-35) was designated water absorbing resin (2-35A), the one obtained from water absorbing resin (2-40) water absorbing resin (2-40A), and the one obtained from water absorbing resin (2-45) water absorbing resin (2-45A).

Table 2 shows measurements of the CRC, AAP, SFC, D50, and ratio of particles of such sizes that they could pass through a sieve having a mesh opening size of –150 μam for water absorbing resins (2-35A), (2-40A), and (2-45A).

Example 3

436.4 g of an acrylic acid, 4617.9 g of a 37 mass % aqueous solution of sodium acrylate, 372.6 g of pure water, and 10.13 g of polyethylene glycol diacrylate (weight-average molecular weight Mw 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 38.76 g of a 10 mass % aqueous solution of sodium persulfate and 24.22 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. After the polymerization started, it took not longer than 15 minutes to reach a maximum temperature. The resulting water-containing gel (water-containing gel-like crosslinked polymer) had been comminuted to a diameter of about 5 mm or less.

The water-containing gel contained 0.0591 mass % thermally decomposing radical initiator (=Ci mass %) and 41.4 mass % solid content (=Cm mass %). The thermally decomposing radical initiator content index was 53.1. These results are shown in Table 1.

The comminuted water-containing gel-like crosslinked polymer was spread on a 50-mesh metal net and dried in hot wind at 180° C. for 45 minutes. The dried substance was pulverized in a roll mill and subjected to a classification using a JIS-standard sieve having a mesh opening size of 710 μm. Those particles which had passed through that sieve were then passed through a JIS-standard sieve having a mesh opening size of 175 μm for further classification. The fine particles having passed through the sieve were removed to obtain water absorbing resin (3) which had an irregularly pulverized shape. Resin (3) had a mass-average particle diameter D50 of 339 μm. The logarithmic standard deviation, σζ, of the particle size distribution of resin (3) was 0.33. Water absorbing resin (3) had a centrifuge retention capacity CRC of 34.8 g/g and contained 7.3 mass % extractable polymer content. The particles of such sizes that they could pass through a sieve having a mesh opening size of 150 μm accounted for 1.7 mass % of resin (3).

100 mass parts of obtained water absorbing resin (3) was evenly mixed with a surface crosslinking agent that was a mixed solution of 0.38 mass part 1,4-butanediol, 0.63 mass part propylene glycol, 3.39 mass part pure water, and 0.1 mass part sodium persulfate. After the mixing, the mixture was heat treated at 212° C. Sample mixtures were prepared with different heating times: 40 minutes, 45 minutes, and 50 minutes. Thereafter, the resulting particle samples were disintegrated until they could pass through a JIS-standard sieve having a mesh opening size of 710 μm. Next, the disintegrated particle samples were subjected to paint shaker test 1, to obtain surface-crosslinked water absorbing resins: the one heated for 40 minutes was designated water absorbing resin (3-40), the one heated for 45 minutes water absorbing resin (3-45), and the one heated for 50 minutes water absorbing resin (3-50).

A mixed solution of 0.40 mass parts of a 27.5 mass % aqueous solution of aluminum sulfate (equivalent to 8 mass % aluminum oxide), 0.134 mass parts of a 60 mass % aqueous solution of sodium lactate, and 0.002 mass part propylene glycol was added to the surface-crosslinked water absorbing resins (3-40), (3-45), and (3-50) each 100 mass parts. After the addition, the mixtures were dried in a windless environment for 1 hour at 60° C. Following the drying, these particle samples were disintegrated until they could pass through a JIS-standard sieve having a mesh opening size of 710 μm. Next, the disintegrated particle samples were subjected to paint shaker test 2, to obtain water absorbing resins: the one obtained from water absorbing resin (3-40) was designated water absorbing resin (3-40A), the one obtained from water absorbing resin (3-45) water absorbing resin (3-45A), and the one obtained from water absorbing resin (3-50) water absorbing resin (3-50A).

Table 2 shows measurements of the CRC, AAP, SFC, D50, and ratio of particles of such sizes that they could pass through a sieve having a mesh opening size of 150 μm for water absorbing resins (3-40A), (3-45A), and (3-50A).

Example 4

436.4 g of an acrylic acid, 4617.9 g of a 37 mass % aqueous solution of sodium acrylate, 362.9 g of pure water, and 10.13 g of polyethylene glycol diacrylate (weight-average molecular weight Mw 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 48.45 g of a 10 mass % aqueous solution of sodium persulfate and 24.22 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. After the polymerization started, it took not longer than 15 minutes to reach a maximum temperature. The resulting water-containing gel (water-containing gel-like crosslinked polymer) had been comminuted to a diameter of about 5 mm or less.

The water-containing gel contained 0.0826 mass % thermally decomposing radical initiator (=Ci mass %) and 41.2 mass % solid content (=Cm mass %). The thermally decomposing radical initiator content index was 74.6. These results are shown in Table 1.

The comminuted water-containing gel-like crosslinked polymer was spread on a 50-mesh metal net and dried in hot wind at 180° C. for 45 minutes. The dried substance was pulverized in a roll mill and subjected to a classification using a JIS-standard sieve having a mesh opening size of 710 µm. Those particles which had passed through that sieve were then passed through a JIS-standard sieve having a mesh opening size of 175 µm for further classification. The fine particles having passed through the sieve were removed to obtain water absorbing resin (4) which had an irregularly pulverized shape. Resin (4) had a mass-average particle diameter D50 of 341 µm. The logarithmic standard deviation, σζ, of the particle size distribution of resin (4) was 0.33. Water absorbing resin (4) had a centrifuge retention capacity CRC of 34.8 g/g and contained 7.8 mass % extractable polymer content. The particles of such sizes that they could pass through a sieve having a mesh opening size of 150 µm accounted for 1.8 mass % of resin (4).

100 mass parts of obtained water absorbing resin (4) was evenly mixed with a surface crosslinking agent that was a mixed solution of 0.38 mass part 1,4-butanediol, 0.63 mass part propylene glycol, 3.39 mass part pure water, and 0.1 mass part sodium persulfate. After the mixing, the mixture was heat treated at 212° C. Sample mixtures were prepared with different heating times: 35 minutes, 40 minutes, and 45 minutes. Thereafter, the resulting particle samples were disintegrated until they could pass through a JIS-standard sieve having a mesh opening size of 710 µm. Next, the disintegrated particle samples were subjected to paint shaker test 1, to obtain surface-crosslinked water absorbing resins: the one heated for 35 minutes was designated water absorbing resin (4-35), the one heated for 40 minutes water absorbing resin (4-40), and the one heated for 45 minutes water absorbing resin (4-45).

A mixed solution of 0.40 mass parts of a 27.5 mass % aqueous solution of aluminum sulfate (equivalent to 8 mass % aluminum oxide), 0.134 mass parts of a 60 mass % aqueous solution of sodium lactate, and 0.002 mass part propylene glycol was added to the surface-crosslinked water absorbing resins (4-35), (4-40), and (4-45) each 100 mass parts. After the addition, the mixtures were dried in a windless environment for 1 hour at 60° C. Following the drying, these particle samples were disintegrated until they could pass through a JIS-standard sieve having a mesh opening size of 710 µm. Next, the disintegrated particle samples were subjected to paint shaker test 2, to obtain water absorbing resins: the one obtained from water absorbing resin (4-35) was designated water absorbing resin (4-35A), the one obtained from water absorbing resin (4-40) water absorbing resin (4-40A), and the one obtained from water absorbing resin (4-45) water absorbing resin (4-45A).

Table 2 shows measurements of the CRC, AAP, SFC, D50, and ratio of particles of such sizes that they could pass through a sieve having a mesh opening size of 150 µm for water absorbing resins (4-35A), (4-40A), and (4-45A).

Example 5

436.4 g of an acrylic acid, 4617.9 g of a 37 mass % aqueous solution of sodium acrylate, 378.7 g of pure water, and 8.87 g of polyethylene glycol diacrylate (weight-average molecular weight Mw 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 33.91 g of a 10 mass % aqueous solution of sodium persulfate and 24.22 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. After the polymerization started, it took not longer than 15 minutes to reach a maximum temperature. The resulting water-containing gel (water-containing gel-like crosslinked polymer) had been comminuted to a diameter of about 5 mm or less.

The water-containing gel contained 0.0510 mass % thermally decomposing radical initiator (=Ci mass %) and 40.7 mass % solid content (=Cm mass %). The thermally decomposing radical initiator content index was 46.6. These results are shown in Table 1.

The comminuted water-containing gel-like crosslinked polymer was spread on a 50-mesh metal net and dried in hot wind at 180° C. for 45 minutes. The dried substance was pulverized in a roll mill and subjected to a classification using a JIS-standard sieve having a mesh opening size of 710 µm. Those particles which had passed through that sieve were then passed through a JIS-standard sieve having a mesh opening size of 175 µm for further classification. The fine particles having passed through the sieve were removed to obtain water absorbing resin (5) which had an irregularly pulverized shape. Resin (5) had a mass-average particle diameter D50 of 340 µm. The logarithmic standard deviation, σζ, of the particle size distribution of resin (5) was 0.33. Water absorbing resin (5) had a centrifuge retention capacity CRC of 36.9 g/g and contained 9.2 mass % extractable polymer content. The particles of such sizes that they could pass through a sieve having a mesh opening size of 150 µm accounted for 1.7 mass % of resin (5).

100 mass parts of obtained water absorbing resin (5) was evenly mixed with a surface crosslinking agent that was a mixed solution of 0.38 mass part 1,4-butanediol, 0.63 mass part propylene glycol, and 2.74 mass part pure water. After the mixing, the mixture was heat treated at 212° C. Sample mixtures were prepared with different heating times: 40 minutes and 45 minutes. Thereafter, the resulting particle samples were disintegrated until they could pass through a JIS-standard sieve having a mesh opening size of 710 µm. Next, the disintegrated particle samples were subjected to paint shaker test 1, to obtain surface-crosslinked water absorbing resins: the one heated for 40 minutes was designated water absorbing resin (5-40), and the one heated for 45 minutes water absorbing resin (5-45).

A mixed solution of 0.40 mass parts of a 27.5 mass % aqueous solution of aluminum sulfate (equivalent to 8 mass % aluminum oxide), 0.134 mass parts of a 60 mass % aqueous solution of sodium lactate, and 0.002 mass part propylene glycol was added to the surface-crosslinked water absorbing resins (5-40) and (5-45) each 100 mass parts. After the addition, the mixtures were dried in a windless environment for 1 hour at 60° C. Following the drying, these particle samples were disintegrated until they could pass through a JIS-standard sieve having a mesh opening size of 710 µm. Next, the disintegrated particle samples were subjected to paint shaker test 2, to obtain water absorbing resins: the one obtained from water absorbing resin (5-40) was designated water absorbing resin (5-40A), and the one obtained from water absorbing resin (5-45) water absorbing resin (5-45A).

Table 2 shows measurements of the CRC, AAP, SFC, D50, and ratio of particles of such sizes that they could pass through a sieve having a mesh opening size of 150 μm for water absorbing resins (5-40A) and (5-45A).

Comparative Example 1

436.4 g of an acrylic acid, 4617.9 g of a 37 mass % aqueous solution of sodium acrylate, 381.0 g of pure water, and 11.40 g of polyethylene glycol diacrylate (weight-average molecular weight Mw 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 29.07 g of a 10 mass % aqueous solution of sodium persulfate and 24.22 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. After the polymerization started, it took not longer than 15 minutes to reach a maximum temperature. The resulting water-containing gel (water-containing gel-like crosslinked polymer) had been comminuted to a diameter of about 5 mm or less.

The water-containing gel contained 0.0381 mass % thermally decomposing radical initiator (=Ci mass %) and 40.9 mass % solid content (=Cm mass %). The thermally decomposing radical initiator content index was 34.6. These results are shown in Table 1.

The comminuted water-containing gel-like crosslinked polymer was spread on a 50-mesh metal net and dried in hot wind at 180° C. for 45 minutes. The dried substance was pulverized in a roll mill and subjected to a classification using a JIS-standard sieve having a mesh opening size of 710 μm. Those particles which had passed through that sieve were then passed through a JIS-standard sieve having a mesh opening size of 175 μm for further classification. The fine particles having passed through the sieve were removed to obtain comparative water absorbing resin (1) which had an irregularly pulverized shape. Comparative resin (1) had a mass-average particle diameter D50 of 342 μm. The logarithmic standard deviation, σζ, of the particle size distribution of comparative resin (1) was 0.33. Comparative water absorbing resin (1) had a centrifuge retention capacity CRC of 33.3 g/g and contained 7.4 mass % extractable polymer content. The particles of such sizes that they could pass through a sieve having a mesh opening size of 150 μm accounted for 1.7 mass % of comparative resin (1). Table 3 shows measurements by the aforementioned method of the intrinsic viscosity IV and the weight-average molecular weight Mw for comparative water absorbing resin (1) at such a weight-average molecular weight Mw that Log(Mw)=6.10.

100 mass parts of obtained comparative water absorbing resin (1) was evenly mixed with a surface crosslinking agent that was a mixed solution of 0.38 mass part 1,4-butanediol, 0.63 mass part propylene glycol, and 2.74 mass part pure water. After the mixing, the mixture was heat treated at 212° C. Sample mixtures were prepared with different heating times: 25 minutes, 30 minutes, and 35 minutes. Thereafter, the resulting particle samples were disintegrated until they could pass through a JIS-standard sieve having a mesh opening size of 710 μm. Next, the disintegrated particle samples were subjected to paint shaker test 1, to obtain surface-crosslinked comparative water absorbing resins: the one heated for 25 minutes was designated comparative water absorbing resin (1-25), the one heated for 30 minutes comparative water absorbing resin (1-30), and the one heated for 35 minutes comparative water absorbing resin (1-35). Table 3 shows measurements by the aforementioned method of the intrinsic viscosity IV and the weight-average molecular weight Mw for comparative water absorbing resins (1-25) and (1-35) at such a weight-average molecular weight Mw that Log (Mw)=6.10.

A mixed solution of 0.40 mass parts of a 27.5 mass % aqueous solution of aluminum sulfate (equivalent to 8 mass % aluminum oxide), 0.134 mass parts of a 60 mass % aqueous solution of sodium lactate, and 0.002 mass part propylene glycol was added to surface-crosslinked comparative water absorbing resins (1-25), (1-30), and (1-35) each 100 mass parts. After the addition, the mixtures were dried in a windless environment for 1 hour at 60° C. Following the drying, these particle samples were disintegrated until they could pass through a JIS-standard sieve having a mesh opening size of 710 μm. Next, the disintegrated particle samples were subjected to paint shaker test 2, to obtain water absorbing resins: the one obtained from comparative water absorbing resin (1-25) was designated water absorbing resin (1-25A), the one obtained from comparative water absorbing resin (1-30) water absorbing resin (1-30A), and the one obtained from comparative water absorbing resin (1-35) water absorbing resin (1-35A).

Table 2 shows measurements of the CRC, AAP, SFC, D50, and ratio of particles of such sizes that they could pass through a sieve having a mesh opening size of 150 μm for comparative water absorbing resins (1-25A), (1-30A), and (1-35A).

Comparative Example 2

436.4 g of an acrylic acid, 4617.9 g of a 37 mass % aqueous solution of sodium acrylate, 385.9 g of pure water, and 11.40 g of polyethylene glycol diacrylate (weight-average molecular weight Mw 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 24.22 g of a 10 mass % aqueous solution of sodium persulfate and 24.22 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. After the polymerization started, it took not longer than 15 minutes to reach a maximum temperature. The resulting water-containing gel (water-containing gel-like crosslinked polymer) had been comminuted to a diameter of about 5 mm or less.

The water-containing gel contained 0.0319 mass % thermally decomposing radical initiator (=Ci mass %) and 40.8 mass % solid content (=Cm mass %). The thermally decomposing radical initiator content index was 29.1. These results are shown in Table 1.

The comminuted water-containing gel-like crosslinked polymer was spread on a 50-mesh metal net and dried in hot wind at 180° C. for 45 minutes. The dried substance was pulverized in a roll mill and subjected to a classification using a JIS-standard sieve having a mesh opening size of 710 μm. Those particles which had passed through that sieve were then passed through a JIS-standard sieve having a mesh opening size of 175 μm for further classification. The fine particles having passed through the sieve were removed to obtain comparative water absorbing resin (2) which had an irregularly pulverized shape. Comparative resin (2) had a mass-average particle diameter D50 of 340 μm. The logarithmic standard deviation, σζ, of the particle size distribution of comparative resin (2) was 0.33. Comparative water absorbing resin (2) had a centrifuge retention capacity CRC of 33.2 g/g and contained 7.4 mass % extractable polymer content. The particles of such sizes that they could pass through a sieve having a mesh opening size of 150 μm accounted for 1.6 mass % of comparative resin (2). Table 3 shows measurements by the aforementioned method of the intrinsic viscosity IV and the weight-average molecular weight Mw for comparative water absorbing resin (2) at such a weight-average molecular weight Mw that Log(Mw)=6.10.

100 mass parts of obtained comparative water absorbing resin (2) was evenly mixed with a surface crosslinking agent that was a mixed solution of 0.38 mass part 1,4-butanediol, 0.63 mass part propylene glycol, and 2.74 mass part pure water. After the mixing, the mixture was heat treated at 212.degree. C. Sample mixtures were prepared with different heating times: 30 minutes, 40 minutes, and 45 minutes. Thereafter, the resulting particle samples were disintegrated until they could pass through a JIS-standard sieve having a mesh opening size of 710 μm. Next, the disintegrated particle samples were subjected to paint shaker test 1, to obtain surface-crosslinked comparative water absorbing resins: the one heated for 30 minutes was designated comparative water absorbing resin (2-30), the one heated for 40 minutes comparative water absorbing resin (2-40), and the one heated for 45 minutes comparative water absorbing resin (2-45).

A mixed solution of 0.40 mass parts of a 27.5 mass % aqueous solution of aluminum sulfate (equivalent to 8 mass % aluminum oxide), 0.134 mass parts of a 60 mass % aqueous solution of sodium lactate, and 0.002 mass part propylene glycol was added to surface-crosslinked comparative water absorbing resins (2-30), (2-40), and (2-45) each 100 mass parts. After the addition, the mixtures were dried in a windless environment for 1 hour at 60° C. Following the drying, these particle samples were disintegrated until they could pass through a JIS-standard sieve having a mesh opening size of 710 μm. Next, the disintegrated particle samples were subjected to paint shaker test 2, to obtain water absorbing resins: the one obtained from comparative water absorbing resin (2-30) was designated water absorbing resin (2-30A), the one obtained from comparative water absorbing resin (2-40) water absorbing resin (2-40A), and the one obtained from comparative water absorbing resin (2-45) water absorbing resin (2-45A).

Table 2 shows measurements of the CRC, AAP, SFC, D50, and ratio of particles of such sizes that they could pass through a sieve having a mesh opening size of 150 μm for comparative water absorbing resins (2-30A), (2-40A), and (2-45A).

Comparative Example 3

436.4 g of an acrylic acid, 4617.9 g of a 37 mass % aqueous solution of sodium acrylate, 382.3 g of pure water, and 10.13 g of polyethylene glycol diacrylate (weight-average molecular weight Mw 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 29.07 g of a 10 mass % aqueous solution of sodium persulfate and 24.22 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. After the polymerization started, it took not longer than 15 minutes to reach a maximum temperature. The resulting water-containing gel (water-containing gel-like crosslinked polymer) had been comminuted to a diameter of about 5 mm or less.

The water-containing gel contained 0.0403 mass % thermally decomposing radical initiator (=Ci mass %) and 41.4 mass % solid content (=Cm mass %). The thermally decomposing radical initiator content index was 36.2. These results are shown in Table 1.

The comminuted water-containing gel-like crosslinked polymer was spread on a 50-mesh metal net and dried in hot wind at 180° C. for 45 minutes. The dried substance was pulverized in a roll mill and subjected to a classification using a JIS-standard sieve having a mesh opening size of 710 μm. Those particles which had passed through that sieve were then passed through a JIS-standard sieve having a mesh opening size of 175 μm for further classification. The fine particles having passed through the sieve were removed to obtain comparative water absorbing resin (3) which had an irregularly pulverized shape. Comparative resin (3) had a mass-average particle diameter D50 of 341 μm. The logarithmic standard deviation, σζ, of the particle size distribution of comparative resin (3) was 0.33. Comparative water absorbing resin (3) had a centrifuge retention capacity CRC of 34.7 g/g and contained 7.1 mass % extractable polymer content. The particles of such sizes that they could pass through a sieve having a mesh opening size of 150 μm accounted for 1.7 mass % of comparative resin (3).

100 mass parts of obtained comparative water absorbing resin (3) was evenly mixed with a surface crosslinking agent that was a mixed solution of 0.38 mass part 1,4-butanediol, 0.63 mass part propylene glycol, 3.39 mass part pure water, and 0.1 mass part sodium persulfate. After the mixing, the mixture was heat treated at 212.degree. C. Sample mixtures were prepared with different heating times: 35 minutes, 40 minutes, and 45 minutes. Thereafter, the resulting particle samples were disintegrated until they could pass through a JIS-standard sieve having a mesh opening size of 710 μm. Next, the disintegrated particle samples were subjected to paint shaker test 1, to obtain surface-crosslinked comparative water absorbing resins: the one heated for 35 minutes was designated comparative water absorbing resin (3-35), the one heated for 40 minutes comparative water absorbing resin (3-40), and the one heated for 45 minutes comparative water absorbing resin (3-45).

A mixed solution of 0.40 mass parts of a 27.5 mass % aqueous solution of aluminum sulfate (equivalent to 8 mass % aluminum oxide), 0.134 mass parts of a 60 mass % aqueous solution of sodium lactate, and 0.002 mass part propylene glycol was added to surface-crosslinked comparative water absorbing resins (3-35), (3-40), and (3-45) each 100 mass parts. After the addition, the mixtures were dried in a windless environment for 1 hour at 60° C. Following the drying, these particle samples were disintegrated until they could pass through a JIS-standard sieve having a mesh opening size of 710 μm. Next, the disintegrated particle samples were subjected to paint shaker test 2, to obtain water absorbing resins:

the one obtained from comparative water absorbing resin (3-35) was designated water absorbing resin (3-35A), the one obtained from comparative water absorbing resin (3-40) water absorbing resin (3-40A), and the one obtained from comparative water absorbing resin (3-45) water absorbing resin (3-45A).

Table 2 shows measurements of the CRC, AAP, SFC, D50, and ratio of particles of such sizes that they could pass through a sieve having a mesh opening size of 150 μm for comparative water absorbing resins (3-35A), (3-40A), and (0.3-45A).

Comparative Example 4

436.4 g of an acrylic acid, 4617.9 g of a 37 mass % aqueous solution of sodium acrylate, 384.8 g of pure water, and 7.60 g of polyethylene glycol diacrylate (weight-average molecular weight Mw 523) were dissolved in a reactor which was a lidded double-arm stainless steel kneader (internal volume 10 liters) equipped with two sigma-type blades and a jacket, to prepare a reaction solution. Next, the reaction solution was deaerated in a nitrogen gas atmosphere for 20 minutes. Subsequently, 29.07 g of a 10 mass % aqueous solution of sodium persulfate and 24.22 g of a 0.1 mass % aqueous solution of L-ascorbic acid were added to the reaction solution while stirring, about 25 seconds after which polymerization started. The polymerization was let to proceed at 25° C. to 95° C. inclusive, while crushing the produced gel. The water-containing gel-like crosslinked polymer was removed 30 minutes into the polymerization. After the polymerization started, it took not longer than 15 minutes to reach a maximum temperature. The resulting water-containing gel (water-containing gel-like crosslinked polymer) had been comminuted to a diameter of about 5 mm or less.

The water-containing gel contained 0.0384 mass % thermally decomposing radical initiator (=Ci mass %) and 41.1 mass % solid content (=Cm mass %). The thermally decomposing radical initiator content index was 34.7. These results are shown in Table 1.

The comminuted water-containing gel-like crosslinked polymer was spread on a 50-mesh metal net and dried in hot wind at 180° C. for 45 minutes. The dried substance was pulverized in a roll mill and subjected to a classification using a JIS-standard sieve having a mesh opening size of 710 μm. Those particles which had passed through that sieve were then passed through a JIS-standard sieve having a mesh opening size of 175 μm for further classification. The fine particles having passed through the sieve were removed to obtain comparative water absorbing resin (4) which had an irregularly pulverized shape. Comparative resin (4) had a mass-average particle diameter D50 of 341 μm. The logarithmic standard deviation, σζ, of the particle size distribution of comparative resin (4) was 0.33. Comparative water absorbing resin (4) had a centrifuge retention capacity CRC of 39.5 g/g and contained 12.1 mass % extractable polymer content. The particles of such sizes that they could pass through a sieve having a mesh opening size of 150 μm accounted for 1.6 mass % of comparative resin (4).

100 mass parts of obtained comparative water absorbing resin (4) was evenly mixed with a surface crosslinking agent that was a mixed solution of 0.38 mass part 1,4-butanediol, 0.63 mass part propylene glycol, and 2.74 mass part pure water. After the mixing, the mixture was heat treated at 212° C. Sample mixtures were prepared with different heating times: 45 minutes and 50 minutes. Thereafter, the resulting particle samples were disintegrated until they could pass through a JIS-standard sieve having a mesh opening size of 710 μm. Next, the disintegrated particle samples were subjected to paint shaker test 1, to obtain surface-crosslinked comparative water absorbing resins: the one heated for 45 minutes was designated comparative water absorbing resin (4-45), and the one heated for 50 minutes comparative water absorbing resin (4-50).

A mixed solution of 0.40 mass parts of a 27.5 mass % aqueous solution of aluminum sulfate (equivalent to 8 mass % aluminum oxide), 0.134 mass parts of a 60 mass % aqueous solution of sodium lactate, and 0.002 mass part propylene glycol was added to surface-crosslinked comparative water absorbing resins (4-45) and (4-50) each 100 mass parts. After the addition, the mixtures were dried in a windless environment for 1 hour at 60° C. Following the drying, these particle samples were disintegrated until they could pass through a JIS-standard sieve having a mesh opening size of 710 μm. Next, the disintegrated particle samples were subjected to paint shaker test 2, to obtain water absorbing resins: the one obtained from comparative water absorbing resin (4-45) was designated water absorbing resin (4-45A), and the one obtained from comparative water absorbing resin (4-50) water absorbing resin (4-50A).

Table 2 shows measurements of the CRC, AAP, SFC, D50, and ratio of particles of such sizes that they could pass through a sieve having a mesh opening size of 150 μm for comparative water absorbing resins (4-45A) and (4-50A).

TABLE 1

| | Internal Crosslinking Agent mol % | Molecular Weight, Mi, of Thermally Decomposing Radical Initiator g/mol | Thermally Decomposing Radical Initiator, Ci, in Water-containing Gel mass % | Mole-Average Molecular Weight, Mm, of Polymerized Monomer g/mol | Solid Content, Cm, in Water-containing Gel mass % | Thermally Decomposing Radical Initiator Content Index |
|---|---|---|---|---|---|---|
| Ex. 1 | 0.09 | 238.1 | 0.0547 | 88.55 | 40.9 | 49.7 |
| Ex. 2 | 0.08 | 238.1 | 0.0504 | 88.55 | 41.2 | 45.5 |
| Ex. 3 | 0.08 | 238.1 | 0.0591 | 88.55 | 41.4 | 53.1 |
| Ex. 4 | 0.08 | 238.1 | 0.0826 | 88.55 | 41.2 | 74.6 |
| Ex. 5 | 0.07 | 238.1 | 0.0510 | 88.55 | 40.7 | 46.6 |
| Comp. Ex. 1 | 0.09 | 238.1 | 0.0381 | 88.55 | 40.9 | 34.6 |
| Comp. Ex. 2 | 0.09 | 238.1 | 0.0319 | 88.55 | 40.8 | 29.1 |
| Comp. Ex. 3 | 0.08 | 238.1 | 0.0403 | 88.55 | 41.4 | 36.2 |
| Comp. Ex. 4 | 0.05 | 238.1 | 0.0384 | 88.55 | 41.1 | 34.7 |

From Table 1, the thermally decomposing radical initiator content indices of the water-containing gels obtained in the examples of the invention ranged from 40 to 100. In contrast, those of the water-containing gels obtained in the comparative examples ranged from 29.1 to 36.2, which was out of the range of the present invention. In other words, the adoption of the step of polymerizing a water-soluble unsaturated monomer 0.06 to 5 mol % of which is composed of an internal crosslinking agent and the step of drying at 100 to 250° C. a water-containing gel which has a thermally decomposing radical initiator content index of 40 to 100 enables the provision of a water absorbing resin with excellent physical properties. Accordingly, the water absorbing resin of the present invention, if used in a water absorbent core, forms a water absorbent core with excellent liquid acquisition rate per unit time and high performance.

differences appear to indicate improvement of the internal structure of the water absorbing resins. In other words, the use of a water absorbing resin of which the intrinsic viscosity IV is 7.3 dL/g or lower after the treatment at such a weight-average molecular weight Mw that Log(Mw)=6.10 enables the provision of a water absorbing resin with excellent physical properties, as can be seen from the results shown in Table 2 and Table 3. Accordingly, the water absorbing resin of the present invention, if used in a water absorbent core, forms a

TABLE 2

| | Water Absorbing Resin | CRC g/g | SFC $10^{-7} \cdot cm^3 \cdot s \cdot g^{-1}$ | AAP g/g | D50 μm | σ ζ | Ratio of Particles Small Enough to Pass through 150-μm Mesh Sieve mass % |
|---|---|---|---|---|---|---|---|
| Ex. 1 | 1-25A | 30.6 | 40 | 24.6 | 343 | 0.33 | 1.5 |
| | 1-35A | 29.4 | 87 | 24.6 | 342 | 0.33 | 1.6 |
| | 1-40A | 28.3 | 117 | 23.5 | 340 | 0.33 | 1.7 |
| Ex. 2 | 2-35A | 30.1 | 58 | 25.0 | 342 | 0.33 | 1.5 |
| | 2-40A | 29.5 | 96 | 24.8 | 340 | 0.33 | 1.5 |
| | 2-45A | 28.8 | 126 | 24.8 | 339 | 0.33 | 1.6 |
| Ex. 3 | 3-40A | 30.1 | 52 | 25.0 | 341 | 0.33 | 1.5 |
| | 3-45A | 29.3 | 72 | 24.8 | 340 | 0.33 | 1.6 |
| | 3-50A | 28.9 | 105 | 24.2 | 339 | 0.33 | 1.6 |
| Ex. 4 | 4-35A | 30.8 | 32 | 24.7 | 343 | 0.33 | 1.6 |
| | 4-40A | 29.8 | 66 | 24.7 | 342 | 0.33 | 1.7 |
| | 4-45A | 28.6 | 96 | 24.1 | 341 | 0.33 | 1.8 |
| Ex. 5 | 5-40A | 29.4 | 70 | 24.5 | 342 | 0.33 | 1.6 |
| | 5-45A | 28.6 | 94 | 24.1 | 340 | 0.33 | 1.7 |
| Comp. Ex. 1 | 1-25A (Comp.) | 29.7 | 54 | 25.5 | 343 | 0.33 | 1.5 |
| | 1-30A (Comp.) | 28.8 | 79 | 25.2 | 342 | 0.33 | 1.6 |
| | 1-35A (Comp.) | 27.5 | 109 | 24.6 | 340 | 0.33 | 1.7 |
| Comp. Ex. 2 | 2-30A (Comp.) | 30.4 | 38 | 25.4 | 342 | 0.33 | 1.5 |
| | 2-40A (Comp.) | 27.7 | 83 | 24.4 | 341 | 0.33 | 1.6 |
| | 2-45A (Comp.) | 26.5 | 108 | 23.8 | 340 | 0.33 | 1.6 |
| Comp. Ex. 3 | 3-35A (Comp.) | 29.4 | 58 | 25.1 | 343 | 0.33 | 1.6 |
| | 3-40A (Comp.) | 28.3 | 97 | 24.9 | 342 | 0.33 | 1.6 |
| | 3-45A (Comp.) | 27.4 | 121 | 24.0 | 340 | 0.33 | 1.7 |
| Comp. Ex. 4 | 4-45A (Comp.) | 29.4 | 40 | 23.5 | 340 | 0.33 | 1.5 |
| | 4-50A (Comp.) | 28.0 | 45 | 22.6 | 340 | 0.33 | 1.6 |

Figure 2:
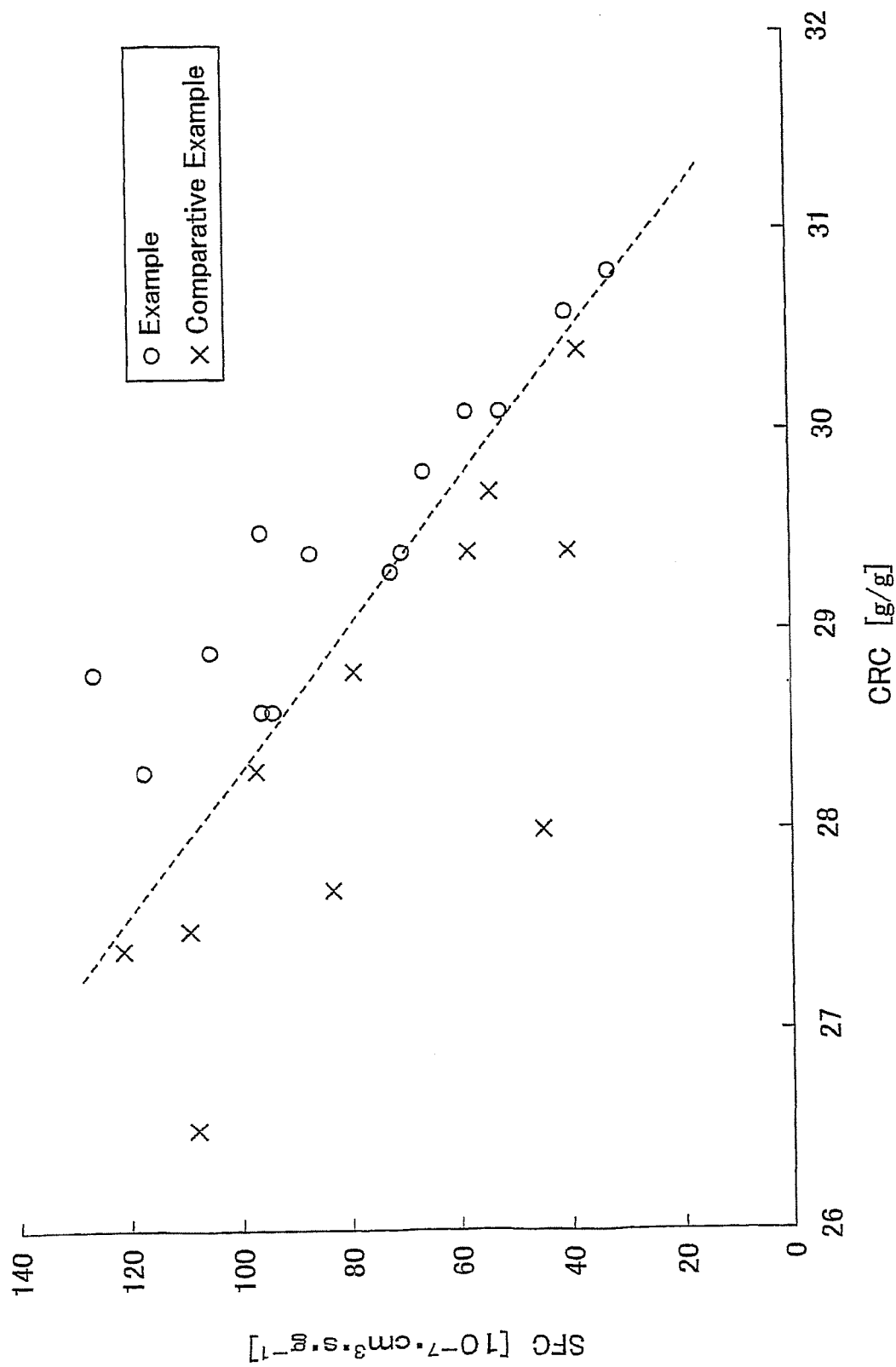
FIG. 2 is a CRC-SFC plot for water absorbing resins obtained in the present examples of the invention and for comparative water absorbing resins obtained in comparative examples.

From Table 2, the water absorbing resins obtained in the examples of the invention had very well-balanced CRCs and SFCs when compared to the comparative water absorbing resins obtained in the comparative examples. This was also evident from the graph in FIG. 2. Accordingly, the water absorbing resin of the present invention, if used in a water absorbent core, forms a water absorbent core with excellent liquid acquisition rate per unit time and high performance.

water absorbent core with excellent liquid acquisition rate per unit time and high performance.

Example 6

258.8 g of an acrylic acid, 1.78 (0.0095 mol %) g of polyethylene glycol diacrylate (weight-average molecular weight Mw 523), and 1.58 g of a 1.0 mass % aqueous solution of

TABLE 3

| | Water Absorbing Resin | IV at Molecular Weight Log(Mw) = 6.10 dL/g | Weight-average Molecular Weight Mw daltons | Log of Weight-average Molecular Weight Log (Mw) |
|---|---|---|---|---|
| Ex. 1 | 1 | 7.06 | $1.053 \times 10^6$ | 6.022 |
| | 1-30 | 7.19 | $1.045 \times 10^6$ | 6.019 |
| | 1-35 | 7.19 | $1.081 \times 10^6$ | 6.034 |
| Comp. Ex. 1 | 1 (Comp.) | 7.35 | $0.988 \times 10^6$ | 5.995 |
| | 1-25 (Comp.) | 7.58 | $1.074 \times 10^6$ | 6.031 |
| | 1-35 (Comp.) | 7.67 | $1.085 \times 10^6$ | 6.035 |
| Comp. Ex. 2 | 2 (Comp.) | 7.37 | $1.116 \times 10^6$ | 6.048 |

From Table 3, the intrinsic viscosities, IV, of the water absorbing resins obtained in the examples of the invention after the treatment at such a weight-average molecular weight Mw that Log(Mw)=6.10 were 7.3 dL/g or lower. Meanwhile, those of the comparative water absorbing resins obtained in the comparative examples were all 7.3 dL/g or higher. These pentasodium diethylenetriaminepentaacetate were mixed in a polypropylene container (internal diameter 80 mm, capacity 1 liter) to prepare solution (A).

210.6 g of a 48.5 mass % aqueous solution of sodium hydroxide and 212.8 g of ion-exchanged water of which the temperature was adjusted to 32° C. were mixed to prepare solution (B). Thereafter, solution (B) was quickly added to and mixed with solution (A) in an open system while stirring with a magnetic stirrer, to prepare a monomer aqueous solution. Neutralization heat and dissolution heat were produced during the course of the mixture; the temperature of the monomer aqueous solution rose to about 102° C.

14.37 g of a 3.75 mass % aqueous solution of sodium persulfate was added when the temperature of the resultant monomer aqueous solution fell from 102° C. to 95° C. After stirring for several seconds, the solution was poured into a tray-type stainless steel container in an open system. The inside of the container was coated with Teflon (Registered Trademark). The tray-type stainless steel container had been heated in advance on a hot plate (Neo Hotplate H1-1000, manufactured by As One Corporation) so that the surface temperature reached 100° C.

The tray-type stainless steel container had a bottom (250 mm×250 mm) and a top (640 mm×640 mm). Its height was 50 mm. The cross-section of the mid-section of the tray-type stainless steel container was trapezoidal. Its top was open.

Soon after the monomer aqueous solution was poured into the tray-type stainless steel container, polymerization started. The polymerization proceeded producing water vapor and expanding in every direction. Thereafter, the content shrank to a size a little larger than the bottom. The expansion and shrink finished in about 1 minute. After being left in the polymerization container for 3 minutes, the water-containing gel-like crosslinked polymer was removed.

The obtained water-containing gel-like crosslinked polymer was crushed using a meat chopper with a dice diameter of 9.5 mm (Royal Meat Chopper VR400K, manufactured by Iidzuka Industries Co., Ltd.) to obtain a comminuted water-containing gel-like crosslinked polymer. In the crushing, the gel was fed at a rate of about 340 g/min, and at the same time deionized water was also added at 48 g/min.

The amount, Ci, of the thermally decomposing radical initiator of the water-containing gel in mass % was 0.0698 mass %. The solid content, Cm, of the water-containing gel in mass % was 50.75 mass %. The thermally decomposing radical initiator content index was 50.7. These results are shown in Table 4.

The comminuted water-containing gel-like crosslinked polymer was spread on a 60-mesh metal net and dried in hot wind at 180° C. for 35 minutes. The dried product was then pulverized in a roll mill and then subjected to a classification using a JIS-standard sieve having a mesh opening size of 710 μm. Those particles that were passed through the sieve were further classified using a JIS-standard, sieve having a mesh opening size of 175 μm to filter out fine particles. The result was water absorbing resin (6) which was irregularly pulverized. Resin (6) was had a mass-average particle diameter D50 of 342 μm. The logarithm standard deviation, σζ, of the particle size distribution of resin (6) was 0.32.

The water absorbing resin (6) had a centrifuge retention capacity CRC of 31.1 g/g and contained a 6.3 mass % extractable polymer content. Resin (6) contained 1.5 mass % particles which could pass through a sieve having a mesh opening size of 150 μm.

100 mass parts of water absorbing resin (6) obtained was evenly mixed with a surface crosslinking agent that was a mixed solution of 0.31 mass parts of 1,4-butanediol, 0.49 mass parts of propylene glycol, and 2.4 mass parts of pure water. The mixture was then heat treated at 212° C. for 35 minutes. Thereafter, obtained particles were subjected to paint shaker test 1, to obtain surface-crosslinked water absorbing resin (6-35).

A solution was added to 100 mass parts of surface-crosslinked water absorbing resin (6-35). The solution was a mixture of 0.80 mass parts of a 27 mass % aqueous solution of aluminum sulfate (equivalent to an 8 mass % aqueous solution of aluminum oxide), 0.134 mass parts of a 60 mass % aqueous solution of sodium lactate, and 0.016 mass parts of propylene glycol. After the addition, the obtained particles were disintegrated until they could pass through a JIS-standard sieve having a mesh opening size of 710 μm. Next, the disintegrated particles were subjected to paint shaker test 2, to obtain water absorbing resin (6-35A).

Example 7

The same process was carried out as in example 6, except that the concentration of the aqueous solution of sodium persulfate was changed from 3.75 mass % to 4.50 mass %.

The amount, Ci, of the thermally decomposing radical initiator of the obtained water-containing gel in mass % was 0.0851 mass %. The solid content, Cm, of the water-containing gel in mass % was 51.02 mass %. The thermally decomposing radical initiator content index was 61.4. These results are shown in Table 4.

The obtained water-containing gel was further processed as in example 6 to obtain irregularly pulverized water absorbing resin (7) which had a mass-average particle diameter D50 of 342 μm. The logarithm standard deviation, σζ, of the particle size distribution of resin (7) was 0.32.

Water absorbing resin (7) had a centrifuge retention capacity CRC of 30.0 g/g and contained a 5.6 mass % extractable polymer content. Resin (7) contained 1.4 mass % particles which could pass through a sieve having a mesh opening size of 150 μm.

Water absorbing resin (7) was further processed as in example 6 to obtain water absorbing resin (7-35A).

Comparative Example 5

The same process was carried out as in example 6, except that the concentration of the aqueous solution of sodium persulfate was changed from 3.75 mass % to 3.00 mass %.

The amount, Ci, of the thermally decomposing radical initiator of the obtained water-containing gel in mass % was 0.0495 mass %. The solid content, Cm, of the water-containing gel in mass % was 50.35 mass %. The thermally decomposing radical initiator content index was 36.2. These results are shown in Table 4.

TABLE 4

| | Internal Crosslinking Agent mol % | Mole-average Molecular Weight, Mi, of Thermally Decomposing Radical Initiator g/mol | Thermally Decomposing Radical Initiator, Ci, in Water-containing Gel mass % | Mole-average Molecular Weight, Mm, of Polymerized Monomer g/mol | Solid Content, Cm, in Water-containing Gel mass % | Thermally Decomposing Radical Initiator Content Index |
|---|---|---|---|---|---|---|
| Ex. 6 | 0.095 | 238.1 | 0.0698 | 87.69 | 50.75 | 50.7 |
| Ex. 7 | 0.095 | 238.1 | 0.0851 | 87.69 | 51.02 | 61.4 |
| Comp. Ex. 5 | 0.095 | 238.1 | 0.0495 | 87.69 | 50.35 | 36.2 |

The obtained water-containing gel was further processed as in example 6 to obtain irregularly pulverized comparative water absorbing resin (5) which had a mass-average particle diameter D50 of 342 μm. The logarithm standard deviation, σζ, of the particle size distribution of resin (5) was 0.32.

Comparative water absorbing resin (5) had a centrifuge retention capacity CRC of 30.6 g/g and contained a 5.6 mass % extractable polymer content. Comparative resin (5) contained 1.6 mass % particles which could pass through a sieve having a mesh opening size of 150 μm.

Comparative water absorbing resin (5) was further processed as in example 6 to obtain water absorbing resin (5-35A).

Table 5 shows measurements of the CRC, AAP, SFC, D50, and ratio of particles of such sizes that they could pass through a sieve having a mesh opening size of 150 μm for water absorbing resins (6-35A) and (7-35A) and comparative water absorbing resin (5-35A).

reduced pressure (1 mmHg or lower) at 60° C. for 12 hours, to prepare comparative water absorbing resin (7).

Comparative Example 8

Water absorbing resin was taken out from a "HUGGIES Ultra Comfort" (size L; lot no. 2005.11.26. TJ0430541128) obtained in June 2006. The water absorbing resin was dried under reduced pressure (1 mmHg or lower) at 60° C. for 12 hours, to prepare comparative water absorbing resin (8).

Comparative Example 9

Water absorbing resin was taken out from "Pampers Let's go" (size 4 maxi; lot no. POL02/02/06 6033 4518 09 22:15)

TABLE 5

| | Water Absorbing Resin | CRC g/g | SFC $10^{-7} \cdot cm^3 \cdot s \cdot g^{-1}$ | AAP g/g | D50 μm | σζ | Small Enough to Pass through 150-μm Mesh Sieve mass % |
|---|---|---|---|---|---|---|---|
| Ex. 6 | 6-35A | 27.0 | 110 | 23.6 | 342 | 0.32 | 1.6 |
| Ex. 7 | 7-35A | 27.1 | 100 | 23.1 | 342 | 0.32 | 1.7 |
| Comp. Ex. 5 | 5-35A (Comp.) | 27.0 | 75 | 23.1 | 342 | 0.32 | 1.6 |
| Comp. Ex. 6 | 6 (Comp.) | 38.0 | 0 | 8.1 | 348 | 0.30 | 0.3 |
| Comp. Ex. 7 | 7 (Comp.) | 35.2 | 0 | 11.0 | 361 | 0.26 | 0.7 |
| Comp. Ex. 8 | 8 (Comp.) | 25.9 | 40 | 21.9 | 345 | 0.50 | 8.3 |
| Comp. Ex. 9 | 9 (Comp.) | 27.8 | 45 | 23.8 | 482 | 0.43 | 2.1 |

Comparative Example 6

Water absorbing resin was taken out from the lower layer (close to the back sheet) of "Refle Wearable Shorts" (thin type; for long time use; size LL; lot no. 40623) obtained in December 2004. The water absorbing resin was used as comparative water absorbing resin (6).

Comparative Example 7

Water absorbing resin was taken out from a "GOO. N" (First Underwear; size L; lot no. 7026281519) obtained in April 2006. The water absorbing resin was dried under obtained in June 2006. The water absorbing resin was dried under reduced pressure (1 mmHg or lower) at 60° C. for 12 hours, to prepare comparative water absorbing resin (9).

Table 6 shows measurements of the weight-average molecular weight Mw, number-average molecular weight Mn, and molecular weight distribution Mw/Mn of water absorbing resins (1-40A), (2-45A), (3-50A), (4-45A), (5-45A), (6-35A), and (7-35A), comparative water absorbing resin (1-30A), (2-40A), (3-40A), (4-50A), (5-35A), (6), (7), and (8), and comparative water absorbing resin (9) obtained above were measured under set 2 of hydrolysis conditions.

TABLE 6

| | Water Absorbing Resin | Molecular Weight Mw under Set 2 of Hydrolysis Conditions daltons | Molecular Weight Mn under Set 2 of Hydrolysis Conditions daltons | Molecular Weight Distribution Mw/Mn under Set 2 of Hydrolysis Conditions | Intrinsic Viscosity IV dl/g |
|---|---|---|---|---|---|
| Ex. 1 | 1-40A | 421,290 | 182,098 | 2.31 | 2.40 |
| Ex. 2 | 2-45A | 382,229 | 161,089 | 2.37 | 2.28 |
| Ex. 3 | 3-50A | 441,134 | 185,754 | 2.37 | 2.45 |
| Ex. 4 | 4-45A | 370,245 | 151,237 | 2.45 | 2.13 |
| Ex. 5 | 5-45A | 370,584 | 151,354 | 2.45 | 2.13 |
| Ex. 6 | 6-35A | 420,621 | 182,980 | 2.30 | 2.33 |
| Ex. 7 | 7-35A | 415,560 | 168,970 | 2.46 | 2.28 |
| Comp. Ex. 1 | 1-30A (Comp.) | 335,858 | 139,468 | 2.41 | 2.02 |
| Comp. Ex. 2 | 2-40A (Comp.) | 315,672 | 136,960 | 2.30 | 1.96 |
| Comp. Ex. 3 | 3-40A (Comp.) | 221,634 | 113,649 | 1.95 | 1.51 |
| Comp. Ex. 4 | 4-50A (Comp.) | 335,672 | 144,979 | 2.32 | 2.02 |
| Comp. Ex. 5 | 5-35A (Comp.) | 356,457 | 126,261 | 2.82 | 2.05 |
| Comp. Ex. 6 | 6 (Comp.) | 266,456 | 148,901 | 1.79 | 1.87 |
| Comp. Ex. 7 | 7 (Comp.) | 273,591 | 121,422 | 2.25 | 1.78 |
| Comp. Ex. 8 | 8 (Comp.) | 292,222 | 125,244 | 2.33 | 1.56 |
| Comp. Ex. 9 | 9 (Comp.) | 350,634 | 136,703 | 2.56 | 1.92 |

Table 7 shows measurements of the weight-average molecular weight Mw, number-average molecular weight Mn, and molecular weight distribution Mw/Mn of the water-soluble components of water absorbing resins (1-40A), (2-45A), (3-50A), (4-45A), (5-45A), (6-35A), and (7-35A) obtained above.

TABLE 7

|  | Water Absorbing Resin | Molecular Weight Mw of Extractable Polymer Content daltons | Molecular Weight Mn of Extractable Polymer Content daltons | Distribution Mw/Mn of Extractable Polymer Content | Intrinsic Viscosity IV of Extractable Polymer Content dl/g |
|---|---|---|---|---|---|
| Ex. 1 | 1-40A | 239,740 | 106,925 | 2.24 | 1.72 |
| Ex. 2 | 2-45A | 259,908 | 116,821 | 2.22 | 1.86 |
| Ex. 3 | 3-50A | 251,342 | 102,897 | 2.44 | 1.81 |
| Ex. 4 | 4-45A | 233,160 | 102,020 | 2.29 | 1.71 |
| Ex. 5 | 5-45A | 228,541 | 99,852 | 2.29 | 1.69 |
| Ex. 6 | 6-35A | 205,095 | 84,050 | 2.44 | 1.51 |
| Ex. 7 | 7-35A | 196,516 | 75,285 | 2.61 | 1.46 |

Example 8

Water absorbing resins (1-40A), (2-45A), (3-50A), (4-45A), (5-45A), (6-35A), and (7-35A) were processed as below.

50 weight parts of the water absorbing resin was dry-mixed with 50 weight parts of wood-crushed pulp in a mixer. Next, the obtained mixture was molded into a web 120 mm×350 mm. The web was pressed under a pressure of 2 kg/cm$^2$ for 5 seconds, to obtain a water absorbent core the basic weight of which was about 500 g/m$^2$.

Subsequently, a back sheet (liquid impermeable sheet), the water absorbent core, and a top sheet (liquid permeable sheet) were attached together in this order using double-sided adhesive tape. The back sheet was made of polypropylene which was impermeable to liquid and had "leg gathers." The top sheet was made of polypropylene which was permeable to liquid. The assembly was then provided with two "tape zippers" to make an absorbing article (that is, a disposable diaper). The absorbing article weighed 44 grams.

The absorbing article was fixed flat on a table. On top of the article were placed a 20-mesh metal net (12×40 cm), an acrylic plate of the same size (equipped at the center with a cylinder 70 mm in diameter for liquid injection), and a load, so that the water absorbent core is under a total load of 20 g/cm$^2$.

75 mL of a 0.9 mass % aqueous solution of sodium chloride, the temperature of which was adjusted to 37° C., was quickly poured into the cylinder. Time (AT) was counted until the liquid was absorbed. The same operation was repeated every 60 minutes (a total of four times).

The times AT1 to AT4 which it took for the liquid be absorbed in the first to fourth observations respectively were summed to obtain a value AT (sec). From this value, a liquid acquisition rate per unit time (AR) was calculated as in the equation below:

$$AR\ (mL/sec)=300/AT$$

Table 8 shows measurements of the AT (sec) and liquid acquisition rate per unit time (AR) of each of the absorbing articles prepared using the above water absorbing resins.

Comparative Example 10

The same process was carried out as in example 8 on each of comparative water absorbing resins (1-30A), (2-40A), (3-40A), (4-50A), (5-35A), (6), (7), (8), and (9). Table 8 shows measurements of the AT (sec) and liquid acquisition rate per unit time (AR) of each of the absorbing articles prepared using the comparative water absorbing resins.

It is understood from Table 8 that the water absorbing resins of the example of the present application, when used as water absorbent cores, exhibit excellent liquid acquisition rates per unit time.

TABLE 8

|  | Water Absorbing Resin | Sum (AT) of Times for Liquid to be Absorbed in Observation 1 to 4 sec | Liquid Acquisition Rate per Unit Time (AR) ml/sec |
|---|---|---|---|
| Ex. 8 | 1-40A | 241 | 1.245 |
| Ex. 8 | 2-45A | 233 | 1.288 |
| Ex. 8 | 3-50A | 240 | 1.250 |
| Ex. 8 | 4-45A | 244 | 1.230 |
| Ex. 8 | 5-45A | 244 | 1.230 |
| Ex. 8 | 6-35A | 245 | 1.224 |
| Ex. 8 | 7-35A | 246 | 1.220 |
| Comp. Ex. 10 | 1-30A (Comp.) | 261 | 1.149 |
| Comp. Ex. 10 | 2-40A (Comp.) | 264 | 1.136 |
| Comp. Ex. 10 | 3-40A (Comp.) | 268 | 1.119 |
| Comp. Ex. 10 | 4-50A (Comp.) | 282 | 1.064 |
| Comp. Ex. 10 | 5-35A (Comp.) | 269 | 1.115 |
| Comp. Ex. 10 | 6 (Comp.) | 335 | 0.896 |
| Comp. Ex. 10 | 7 (Comp.) | 335 | 0.896 |
| Comp. Ex. 10 | 8 (Comp.) | 291 | 1.031 |
| Comp. Ex. 10 | 9 (Comp.) | 279 | 1.075 |

INDUSTRIAL APPLICABILITY

The water absorbing resin and water absorbent core in accordance with the present invention, as well as the water absorbing resin obtained by the method of manufacturing a water absorbing resin in accordance with the present invention, are applicable as water absorbing/retaining agents for various uses because they have excellent water absorption and other properties and produce little dust.

Specific applications may include water absorbing/retaining agents for absorbent articles, such as disposable diapers, sanitary napkins, incontinent pads, and medical pads; agriculture/horticulture water retaining agents, such as bog moss replacements, soil conditioners, water retaining agents, and agricultural chemical enhancers; water retaining agents for construction purposes, such as dew inhibitors for interior wall materials and cement additives; release controlling agent;

cold insulators; disposable pocket stoves; sludge coagulating agents; food freshness retaining agents; ion exchange column materials; sludge/oil dehydrates: desiccants; and humidity conditioning agents.

In addition, the water absorbing resin of the present invention is especially suitable for use in disposable diapers, sanitary napkins, and like sanitary/hygienic materials for absorbing feces, urine, or blood.

The invention claimed is:

1. A water absorbing resin, comprising a water-soluble unsaturated monomer as a repeat unit for a major chain, 90 mol % or more, based on the total monomers making up the resin, of an acrylic acid and/or salt thereof, the resin having an internal crosslinking structure and exhibiting a weight-average molecular weight Mw of 360,000 to 1,000,000 daltons and an intrinsic viscosity IV of 2.1 to 6.0 dL/g where the weight-average molecular weight Mw and the intrinsic viscosity IV are measured after treatment under set 2 of hydrolysis conditions, in which treatment 20 mg of the water absorbing resin is left in 10 grams of a 0.1 mol/L aqueous solution of sodium hydroxide at 80° C. for 3 weeks, and the water absorbing resin regulates a thermally decomposing radical initiator content index for a water-containing gel to 40 to 100.

2. The water absorbing resin of claim 1, wherein the resin shows a molecular weight distribution Mw/Mn after the treatment of 2.0 to 3.0.

3. The water absorbing resin of claim 1, wherein the resin contains extractable polymer content which has a weight-average molecular weight Mw of 150,000 to 500,000 daltons.

4. The water absorbing resin of claim 1, wherein the resin contains extractable polymer content which has an intrinsic viscosity IV of 1.0 to 2.0 dL/g.

5. The water absorbing resin of claim 1, wherein the resin contains extractable polymer content which has a molecular weight distribution Mw/Mn of 2.0 to 3.0.

6. The water absorbing resin of claim 1, wherein: the water absorbing resin has a mass-average particle diameter D50 of 200 to 600 μm; the water absorbing resin contains 0 to 5 mass % particles of such sizes that the particles can pass through a sieve having a mesh opening size of 150 μm; and the water absorbing resin has such a particle size distribution with a logarithm standard deviation σζ of 0.20 to 0.50.

7. The water absorbing resin of claim 1, further containing an α-hydroxy carboxylic acid salt.

* * * * *